US007277166B2

(12) United States Patent
Padmanabhan et al.

(10) Patent No.: US 7,277,166 B2
(45) Date of Patent: Oct. 2, 2007

(54) CYTOMETER ANALYSIS CARTRIDGE OPTICAL CONFIGURATION

(75) Inventors: Aravind Padmanabhan, Plymouth, MN (US); Jay G. Schwichtenberg, New Hope, MN (US); Bernard S. Fritz, Eagan, MN (US); Cleopatra Cabuz, Eden Prairie, MN (US); Ernest A. Satren, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 206 days.

(21) Appl. No.: 10/908,543

(22) Filed: May 16, 2005

(65) Prior Publication Data

US 2005/0243304 A1  Nov. 3, 2005

Related U.S. Application Data

(63) Continuation-in-part of application No. 10/612,664, filed on Jul. 2, 2003, now Pat. No. 7,000,330, which is a continuation-in-part of application No. 10/304,773, filed on Nov. 26, 2002, which is a continuation-in-part of application No. 09/630,924, filed on Aug. 2, 2000, now Pat. No. 6,597,438.

(60) Provisional application No. 60/404,876, filed on Aug. 21, 2002.

(51) Int. Cl.
*G01N 21/01* (2006.01)
*G01N 33/48* (2006.01)
*G01N 1/10* (2006.01)
*G01N 15/02* (2006.01)

(52) U.S. Cl. .................. 356/244; 356/39; 356/246; 356/335

(58) Field of Classification Search ................ 356/39, 356/244, 335
See application file for complete search history.

(56) References Cited

U.S. PATENT DOCUMENTS 3,822,095 A  7/1974  Hirschfeld (Continued)

FOREIGN PATENT DOCUMENTS

DE  10122321  4/2002

(Continued)

OTHER PUBLICATIONS

Altendorf et al, "Results Obtained Using A Prototype Microfluidics-Based Hematology Analyzer", SPIE Biomedical Optics 97, 1997.

(Continued)

*Primary Examiner*—Gregory J. Toatley, Jr.
*Assistant Examiner*—Iyabo S Alli
(74) *Attorney, Agent, or Firm*—Kris T. Fredrick

(57) ABSTRACT

A medium having microfluidic circuitry for sampling and analyses. The medium may be a cartridge having a window countersunk into it and containing a flow channel. The flow channel may have items of interest flowing through it. Analyses of these items may be optical involving one or more light sources emanating light to and one or more light detectors receiving light from the channel. There are various configurations so that source and detector light cones may reach the flow channel without obscuration or interference of the light to and from the flow channel in the window.

26 Claims, 24 Drawing Sheets

U.S. PATENT DOCUMENTS

| | | |
|---|---|---|
| 3,928,094 A | 12/1975 | Angell |
| 3,976,862 A | 8/1976 | Curbelo |
| 4,284,412 A | 8/1981 | Hansen et al. |
| 4,336,029 A | 6/1982 | Natale |
| 4,478,076 A | 10/1984 | Bohrer |
| 4,478,077 A | 10/1984 | Boher |
| 4,501,144 A | 2/1985 | Higashi et al. |
| 4,573,796 A | 3/1986 | Martin et al. |
| 4,599,000 A | 7/1986 | Yasuyoshi |
| 4,651,564 A | 3/1987 | Johnson et al. |
| 4,683,159 A | 7/1987 | Bohrer et al. |
| 4,695,034 A | 9/1987 | Shimizu et al. |
| 4,704,033 A | 11/1987 | Fay et al. |
| 4,745,279 A | 5/1988 | Karkar et al. |
| 4,818,263 A | 4/1989 | Mitch |
| 4,857,451 A | 8/1989 | Schwartz |
| 4,874,949 A | 10/1989 | Harris et al. |
| 4,911,616 A | 3/1990 | Laumann, Jr. |
| 4,932,989 A | 6/1990 | Presby |
| 5,017,497 A | 5/1991 | de Grooth et al. |
| 5,050,429 A | 9/1991 | Nishimoto et al. |
| 5,078,581 A | 1/1992 | Blum et al. |
| 5,082,242 A | 1/1992 | Bonne et al. |
| 5,085,562 A | 2/1992 | van Lintel |
| 5,096,388 A | 3/1992 | Weinberg |
| 5,108,623 A | 4/1992 | Cangelosi et al. |
| 5,129,794 A | 7/1992 | Beatty |
| 5,171,132 A | 12/1992 | Miyazaki et al. |
| 5,176,358 A | 1/1993 | Bonne et al. |
| 5,185,641 A | 2/1993 | Igushi et al. |
| 5,194,909 A | 3/1993 | Tycko |
| 5,219,278 A | 6/1993 | van Lintel |
| 5,224,843 A | 7/1993 | van Lintel |
| 5,244,537 A | 9/1993 | Ohnstein |
| 5,308,772 A | 5/1994 | Sakata et al. |
| 5,314,824 A | 5/1994 | Schwartz |
| 5,323,999 A | 6/1994 | Bonne et al. |
| 5,367,474 A | 11/1994 | Auer et al. |
| 5,441,597 A | 8/1995 | Bonne et al. |
| 5,452,878 A | 9/1995 | Gravesen et al. |
| 5,457,526 A | 10/1995 | Kosaka |
| 5,464,581 A | 11/1995 | Van Den Engh |
| 5,510,267 A | 4/1996 | Marshall |
| 5,528,045 A | 6/1996 | Hoffman et al. |
| 5,570,193 A | 10/1996 | Landa et al. |
| 5,601,080 A | 2/1997 | Oppenheimer |
| 5,616,501 A | 4/1997 | Rodriguez |
| 5,633,724 A | 5/1997 | King et al. |
| 5,683,159 A | 11/1997 | Johnson |
| 5,684,575 A | 11/1997 | Steen |
| 5,716,852 A | 2/1998 | Yager et al. |
| 5,717,631 A | 2/1998 | Carley et al. |
| 5,726,364 A | 3/1998 | Van Den Engh |
| 5,726,751 A | 3/1998 | Altendorf et al. |
| 5,739,902 A | 4/1998 | Gjelsnes et al. |
| 5,747,349 A | 5/1998 | Van Den Engh et al. |
| 5,757,476 A | 5/1998 | Nakamoto et al. |
| 5,760,900 A | 6/1998 | Ito et al. |
| 5,793,485 A | 8/1998 | Gourley |
| 5,799,030 A | 8/1998 | Brenner |
| 5,822,170 A | 10/1998 | Cabuz et al. |
| 5,836,750 A | 11/1998 | Cabuz |
| 5,837,547 A | 11/1998 | Schwartz |
| 5,839,807 A | 11/1998 | Perlo |
| 5,863,502 A | 1/1999 | Southgate et al. |
| 5,880,474 A | 3/1999 | Norton et al. |
| 5,888,823 A | 3/1999 | Matsumoto et al. |
| 5,893,722 A | 4/1999 | Hibbs-Brenner et al. |
| 5,901,939 A | 5/1999 | Cabuz et al. |
| 5,922,210 A | 7/1999 | Brody et al. |
| 5,928,949 A | 7/1999 | Sakata et al. |
| 5,932,100 A | 8/1999 | Yager et al. |
| 5,934,885 A | 8/1999 | Farrell et al. |
| 5,948,684 A | 9/1999 | Weigl et al. |
| 5,970,315 A | 10/1999 | Carley et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,054,335 A | 4/2000 | Sun et al. |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A | 8/2000 | Lievan |
| 6,097,859 A | 8/2000 | Solgaard et al. |
| 6,106,245 A | 8/2000 | Cabuz |
| 6,109,889 A | 8/2000 | Zengerie et al. |
| 6,116,756 A | 9/2000 | Peeters et al. |
| 6,124,663 A | 9/2000 | Haake et al. |
| 6,139,800 A | 10/2000 | Chandler |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,281,975 B1 | 8/2001 | Munk |
| 6,382,228 B1 | 5/2002 | Cabuz et al. |
| 6,549,275 B1 | 4/2003 | Cabuz et al. |
| 6,589,792 B1 | 7/2003 | Malachowski |
| 6,594,009 B2 | 7/2003 | Saccomanno |
| 6,597,438 B1 | 7/2003 | Cabuz et al. |
| 6,618,143 B2 | 9/2003 | Roche et al. |
| 2003/0142291 A1 | 7/2003 | Padmanabhan et al. |
| 2004/0125370 A1* | 7/2004 | Montagu ............... 356/244 |
| 2005/0243304 A1 | 11/2005 | Padmanabhan et al. |

FOREIGN PATENT DOCUMENTS

| | | |
|---|---|---|
| EP | 0269076 | 6/1988 |
| EP | 1001326 | 5/1999 |
| EP | 1134548 | 9/2001 |
| JP | 61066947 | 4/1986 |
| JP | 10073528 | 8/1996 |
| JP | 2000056228 | 7/1999 |
| WO | WO95/27199 | 3/1995 |
| WO | WO99/60397 | 4/1999 |
| WO | WO 01/09598 | 7/2000 |
| WO | WO 02/10713 | 2/2002 |
| WO | WO 02/10714 | 2/2002 |
| WO | 2004048948 | 6/2004 |

OTHER PUBLICATIONS

Altendorf et al., "Differential Blood Cell Counts Obtained Using A Microchannel Based Flow Cytometer", Solid State Sensors & Actuators, vol. 1, 531, 1997.

Altendorf et al., "Implemetation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers '99, Jun. 7-12, 1999, Sendai Japan, p. 1890-1.

Darling et al., "Integration Of Microelectrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches To Immunoassays", SPIE conference on Micromachining and Microfabrication Symposium at Santa Clara, CA, Sep. 20-22, 1999.

http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

http://www.micronics.net/tsensor.htm, 2 pages, downloaded Jun. 14, 2000.

Huang et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Elctromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometry 9:39-43, 1988.

Toshiyoshi et al., "Micromechanical Lens Scanner for Fiber Optic Switches", Pro. 3rd International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE/LEOS International Coference on Optical EMMS/ Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantramont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Weigl et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, μTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", μTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

* cited by examiner

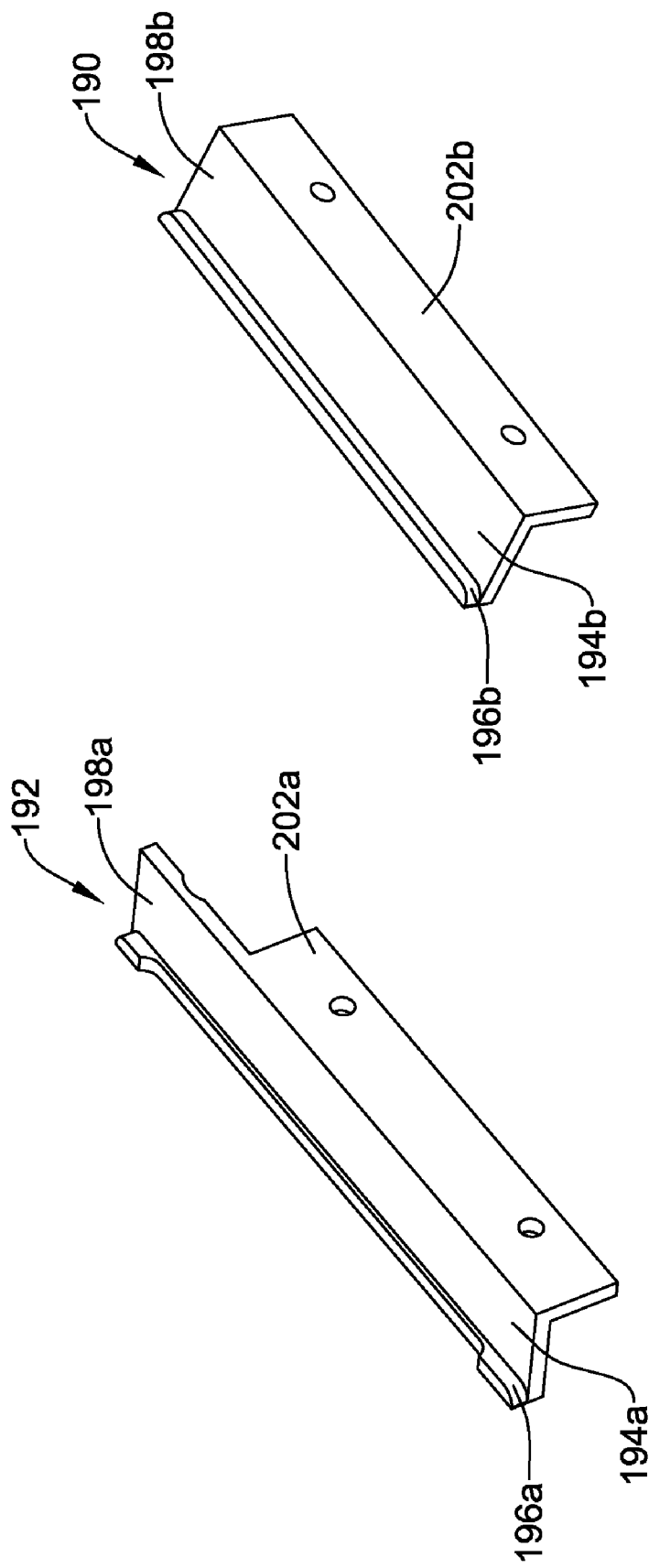

CYTOMETER ANALYSIS CARTRIDGE OPTICAL CONFIGURATION

DESCRIPTION

This present invention is a continuation-in-part of U.S. patent application Ser. No. 10/612,664, filed on Jul. 2, 2003 now U.S. Pat. No. 7,000,330, which claims the benefit of U.S. Provisional Application No. 60/404,876, filed Aug. 21, 2002. This present invention is also a continuation-in-part of U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438, and claims the benefit thereof. The above-mentioned patent documents are incorporated herein by reference.

BACKGROUND

The present invention generally relates to cytometery, and particularly to removable media of a cytometer. More particularly, the invention related to an improvement of the media.

Over the past several decades there has been an ever increasing use of devices and systems that use, in one form or another, a removable media member. Some illustrative removable media members include, for example, removable or replaceable filters, removable ink and toner cartridges, removable data storage devices such as magnetic or optical disks, removable magnetic tape cartridges, removable memory sticks, and so forth.

A limitation of many of the existing systems is that the alignment tolerance between the inserted removable media member and the receiving device is often not very precise. In some cases, the receiving device simply includes a slot for receiving the removable media member. In other cases, a more complex mechanical mechanism is provided, such as the mechanical mechanism used in a conventional video cassette recorder (VCR) for receiving VCR tapes. For some applications, the alignment tolerance that can be achieved using these existing systems is not adequate.

Another limitation with many existing systems is that provisions are typically not made for including one or more electrical or optical devices on or in the removable media member. For some applications, however, it may be desirable to provide one or more electrical and/or optical devices on or in the removable media member. In addition, it may be desirable to provide one or more electrical and/or optical links or connections between the electrical and/or optical devices on or in the removable media and the receiving device so that, for example, various functions may be performed by the removable media member.

SUMMARY

Many advantages may be had by providing methods and apparatus for receiving a removable media member, and more specifically, for providing tighter alignment tolerances between an inserted removable media member and a receiving device. There may also be methods and apparatus for providing one or more electrical or optical device on or in the removable media member itself, and for providing an electrical and/or optical link between the one or more electrical and/or optical devices on or in the removable media and the receiving device.

In a first illustrative example, an apparatus is provided for accepting a removable media member. The apparatus includes a first member and a second member, wherein the first member and the second member are adapted to move away from each other to provide a space for receiving a removable media member. Once the removable media member is inserted into the space, the first member and second member can be moved toward each other to engage and/or secure the removable media member.

In one illustrative example, the first member has one or more L-shaped cleats that provide a slot to receive the removable media member. The L-shaped cleats may include, for example, a first leg that extends away from the first member and toward the second member, and a second leg that extends from a distal end of the first leg and in a perpendicular direction relative to the first leg so that a channel or receiving slot is formed. The channel or receiving slot may then receive at least one side of the removable media member.

In some examples, two L-shaped cleats are provided for providing two spaced channels for receiving opposing sides of the removable media member. That is, the channel or slot of the first L-shaped cleat and the channel or slot of the second L-shaped cleat may be arranged so that the removable media member slides into both channels when it is inserted between the first member and the second member. In one example, the two L-shaped cleats are secured to the first member.

During use, the first member and the second member may be moved away from one another, and the removable media member may be slid into the channel or receiving slots provided by the one or more L-shaped cleats. The L-shaped cleats may be positioned so that that when the removable media member is received by the one or more L-shaped cleats, the removable media member is at least roughly aligned with a desired position relative to the first member and/or second member. The first member and the second member may then be moved toward one another to engage and/or secure the removable media member therebetween.

To remove the removable media member, the first member and the second member may be moved away from each other. Because at least part of the removable media member is positioned in the channel or slot of the one or more L-shaped cleats, and when the one or more L-shaped cleats are secured to the first member, the removable media member may be pulled away from the second member by the L-shaped cleats as the first member and second member are moved away from each other.

To provide better alignment between the removable media member and the first and/or second members, the second member may include one or more alignment pins that extend toward the first member. The removable media member may then include one or more receiving holes for receiving the one or more alignment pins. The alignment pins and receiving holes may provide improved alignment between the removable media member and the first and/or second members when the removable media member is secured between the first member and the second member.

The one or more L-shaped cleats may be used to pull the removable media member away from the second member, thereby separating the one or more receiving holes of the removable media member from the one or more alignment pins that are extending from the second member. With the one or more receiving holes separated from the alignment pins, the removable media member then may be more easily removed from between the first member and the second member.

In some examples, the removable media member may include one or more electrical and/or optical devices. For example, the removable media member may include one or more transistors, diodes, sensors, vertical cavity surface emitting lasers (VCSELs), LEDs, electro-statically actuated actuators or pumps, or any other suitable electrical and/or optical device. To provide power and/or to communicate or control the one or more electrical and/or optical devices, an electrical and/or optical interface may be provided between the first and/or second member and the removable media member.

In one illustrative example, one or more electrical contact pads are provided on a surface of the removable media member. The one or more electrical contact pads may be electrically connected to the one or more electrical and/or optoelectronic devices of the removable media member, such as by a metal trace or the like. In one illustrative example, the first member may include one or more spring biased probes that extend outward away from the first member and toward the second member. The one or more spring biased probes may be positioned to align with the one or more electrical contact pads of the removable media member when the removable media member is at a desired positioned between the first member and the second member. In some cases, the one or more alignment pins discussed above may help provide alignment between the one or more spring biased probes of the first member and the one or more electrical contact pads of the removable media member. When the first member and the second member are moved toward one another to secure and/or engage the removable media member, the one or more spring biased probes of the first member may make electrical contact with the one or more electrical contact pads of the removable media member.

To help separate the one or more spring biased probes of the first member from the one or more electrical contact pads when the first member is moved away from the second member, an outward or separating bias may be provided between the first member and the removable media member. This outward bias may be overcome when the first member and the second member are moved toward each other to secure and/or engage the removable media member. However, when the first member and the second member are moved away from each other to release the removable media member, the outward bias may separate the one or more spring biased probes of the first member from the one or more electrical contact pads, which may make the removal of the removable media member from between the first member and the second member easier and may help protect the spring bias probes from damage.

In another illustrative example, one or more optical transmitters and/or receivers may be provided on a surface of the removable media member. The one or optical transmitters and/or receivers may be electrically connected to the one or more electrical and/or optoelectronic devices of the removable media member, such as by an optical waveguide, metal trace, or the like. In this example, the first member and/or second member may include one or more optical transmitters and or optical receivers, which may be positioned to align with the one or more optical transmitters and/or receivers of the removable media member when the removable media member is at a desired positioned between the first member and the second member. In some cases, the one or more alignment pins discussed above may help provide alignment between the optical transmitters and/or optical receivers of the first and/or second members and the one or more optical transmitters and/or optical receivers of the removable media member. When the first member and the second member are moved toward one another to secure and/or engage the removable media member, the one or more optical transmitters and/or optical receivers of the first and/or second members become aligned with the one or more optical transmitters and/or optical receivers of the removable media member to provide a communications link therebetween.

In some cases, the removable media member may include one or more fluid ports for accepting or delivering fluid to and/or from the removable media member. In one illustrative example, the removable media member may be a fluidic cartridge adapted for use in flow cytometry. The fluidic cartridge may include one or more flow channels. The one or more fluid ports may be in fluid communication with at least some of the flow channels. When so provided, one or more corresponding fluid ports may be provided on the first member and/or second member, as desired. The one or more fluid ports of the first member and/or second member are positioned to align with at least selected ones of the fluid ports of the removable media member when the removable media member is secured and/or engaged by the first member and the second member.

In some cases, one or more alignment pins as discussed above may be provided to help provide alignment between the one or more fluid ports of the first member and/or second member and the one or more fluid ports of the removable media member. In addition, an outward bias may be provided between the removable media member and the first member and/or second member to help separate the one or more fluid ports of the first member and/or second member and the one or more fluid ports of the removable media member when the first member is moved away from the second member.

In some cases, the manufacture of the removable media member may create a ridge, a burr, or other imperfections, particularly around the outer perimeter of the removable media member. In one example, a fluidic cartridge may be manufactured by laminating several layers or sheets together, and then cutting individual fluidic cartridges from the laminated structure. At the cut lines, ridges, burrs, and other imperfections may arise. To help the removable media member seat correctly along the first and/or second member, a groove or other relief structure may provided in receiving surface of the first and/or second member to accommodate the one or more imperfections in the removable media member. In one illustrative example, a groove may extend along a groove path that corresponds to, for example, the perimeter of the removable media member in anticipation of imperfections that might occur along the perimeter of the removable media member. It is contemplated, however, that a groove or other relief structure may be provided at any location where an anticipated imperfection might occur in the removable media member.

BRIEF DESCRIPTION OF THE DRAWING

FIG. 9 is a perspective view of the lower cleat of the first plate or member of FIG. 8;

FIG. 10 is a perspective view of the upper cleat of the first plate or member of FIG. 8;

DESCRIPTION

For illustrative purposes, a portable flow cytometer system is described. Present approaches may have wide applicability to numerous other removable media systems including, for example, removable or replaceable filters, removable ink and toner cartridges, removable data storage devices such as magnetic or optical disks, removable magnetic tape cartridges, removable memory sticks, as well as many other systems and/or devices that use removable media.

Figure 1:
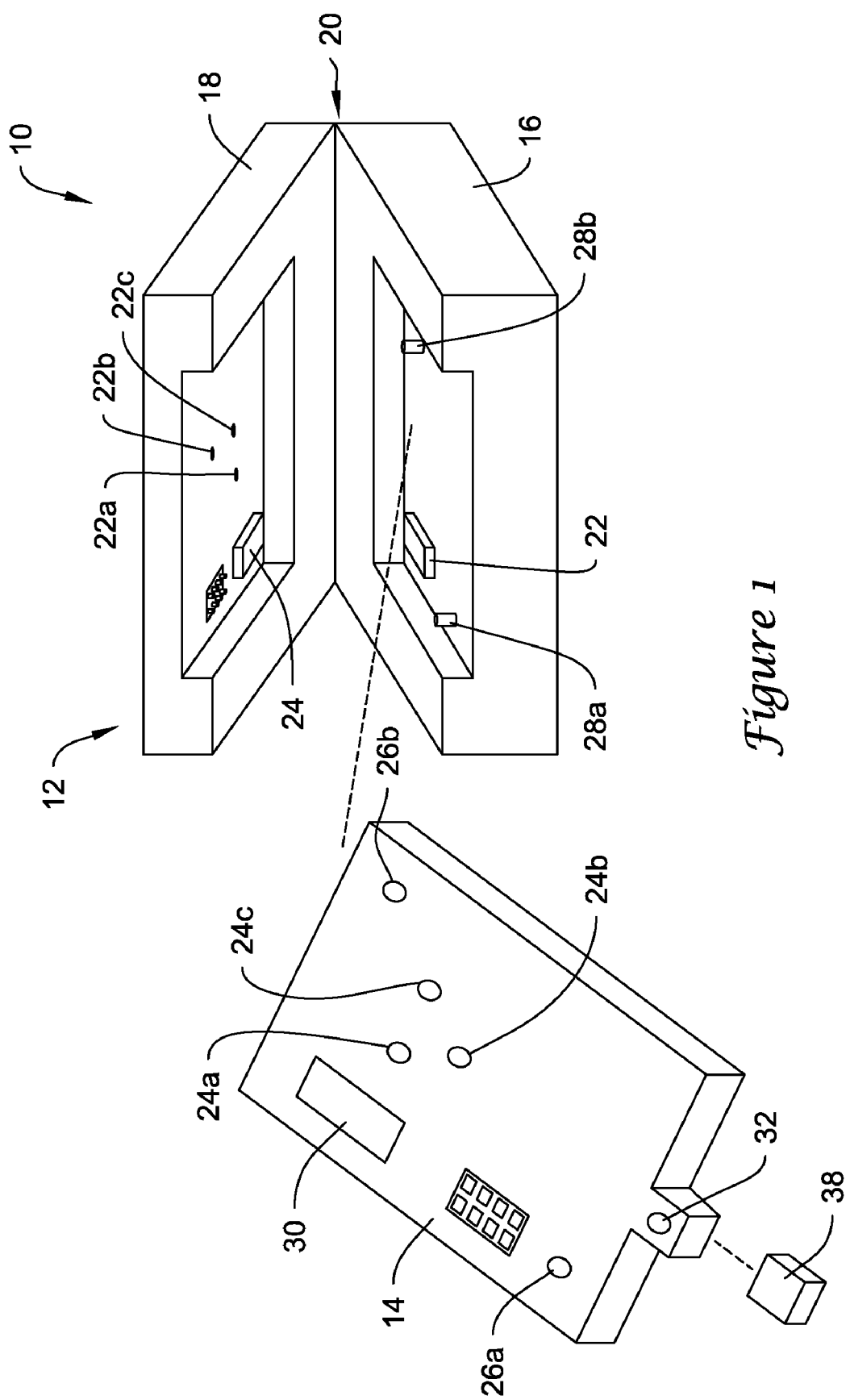
FIG. 1 is a perspective view of an illustrative portable cytometer.

FIG. 1 is a perspective view of an illustrative portable cytometer. The portable cytometer is generally shown at 10, and includes a housing 12 and a removable or replaceable cartridge 14. The removable cartridge 14 may have a front side, a back side, and one or more lateral sides extending between the front side and the back side. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24 with associated optics, as further described in U.S. Pat. No. 6,597,438, issued Jul. 22, 2003, to Cabuz et al., and entitled "Portable Flow Cytometer", and U.S. patent application Ser. No. 6,549,275, issued Apr. 15, 2003, to Cabuz et al., and entitled "Optical Detection System for Flow Cytometry", both of which are incorporated herein by reference.

The removable member (e.g., cartridge) 14 may receive a sample fluid via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed similar to the fluidic circuits available from Micronics Technologies, some of which are fabricated using a laminated structure with etched fluid channels.

The removable cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 may also include a transparent flow stream window 30, which is in alignment with the array of the light sources 22 and light detectors 24. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform differentiation and counting of white blood cells based on light scattering signals received by the light detectors 24. Rather than using a hinged construction for the housing 12, it is contemplated that a sliding cartridge slot or any other suitable construction may be used, including that described further below with respect to FIGS. 5-12.

Figure 2:
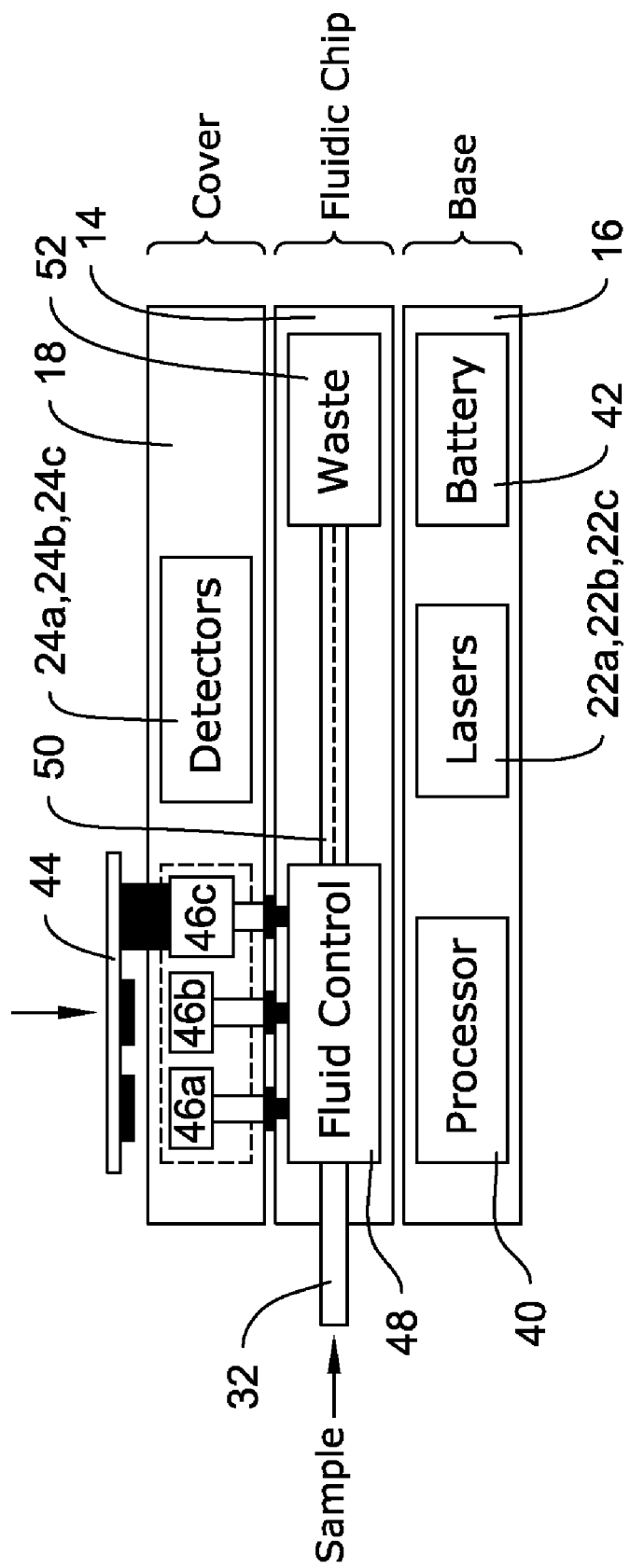
FIG. 2 is a schematic view of the illustrative portable cytometer of FIG. 1.

FIG. 2 is a schematic view of the illustrative portable cytometer of FIG. 1. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and an array of light detectors 24 with associated optics. The removable cartridge 14 may receive a sample fluid via the sample collector port 32. When pressurized by the cover 18, the removable cartridge 14 performs blood dilution, red cell lysing, and hydrodynamic focusing for core formation in an example. Once formed, the core is provided down a flow stream path 50, which passes the flow stream window 30 of FIG. 1. The array of light sources 22 and associated optics in the base provide light through the core stream via the flow stream window 30. The array of light detectors and associated optics receive scattered and non-scattered light from the core, also via the flow stream window 30. The controller or processor 40 receives output signals from the array of detectors, and differentiates and counts selected white blood cells that are present in the core stream.

It is contemplated that the removable cartridge 14 may include a fluid control block 48 for helping to control the velocity of each of the fluids. In the illustrative example, the fluid control block 48 includes flow sensors for sensing the velocity of the various fluids and report the velocities to the controller or processor 40. The controller or processor 40 may then adjust the microvalves associated with pressure-chambers 46a, 46b and 46c to achieve the desired pressures and thus desired fluid velocities for proper operation of the cytometer. In some examples, and as further described below, one or more electrical connections may be provided between the processor 40 in the base 16 and the flow sensors on the removable cartridge 14.

Because blood and other biological waste can spread disease, the removable cartridge 14 may have a waste reservoir 52 downstream of the flow stream window 30. The waste reservoir 52 receives and stores the fluid of the flow stream in the removable cartridge 14. When a test is completed, the removable cartridge may be removed and disposed of, in a container compatible with biological waste.

Figure 3:
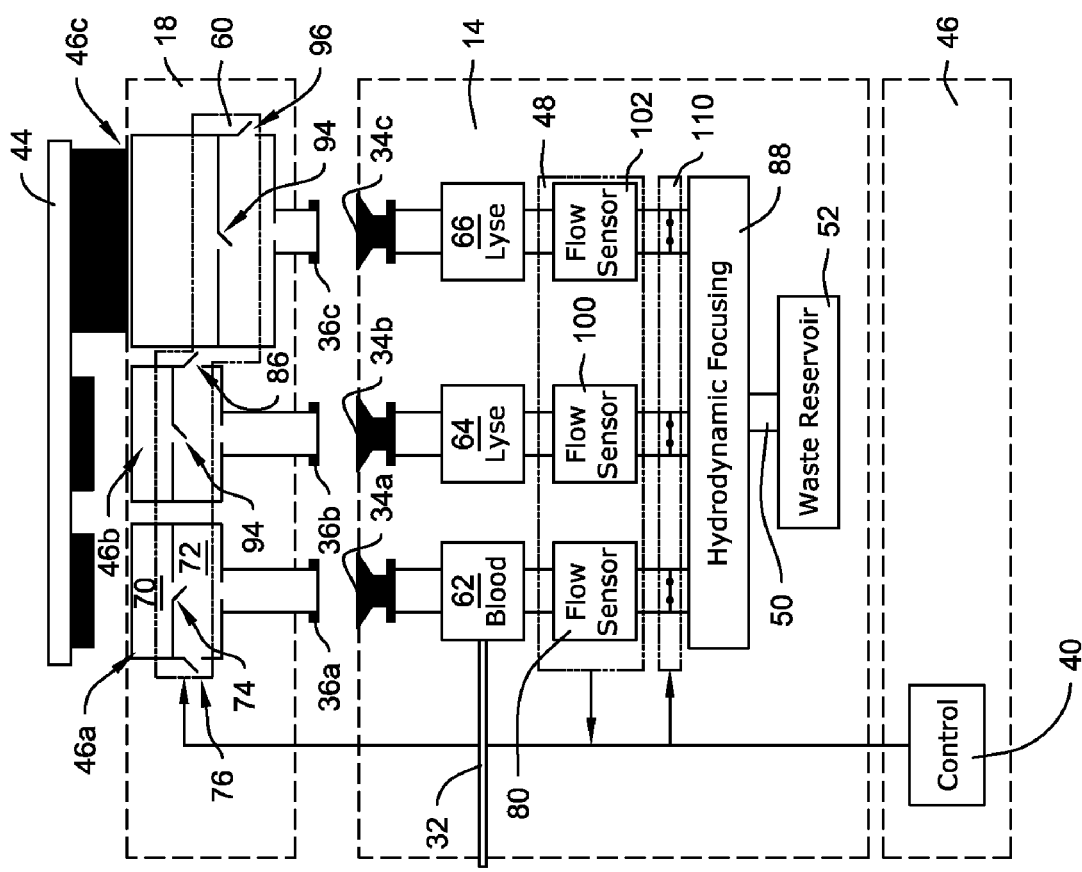
FIG. 3 is a more detailed schematic diagram showing the portable cytometer of FIG. 2 with the cover not yet depressed.
Figure 4:
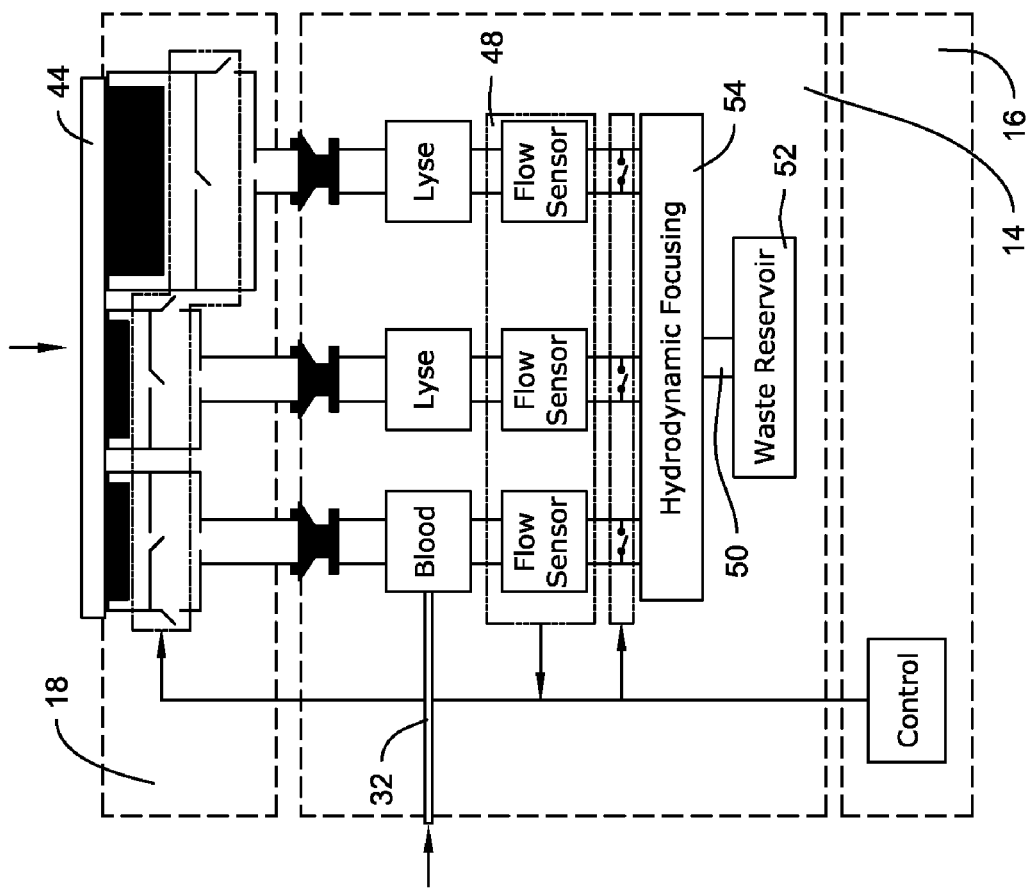
FIG. 4 is a more detailed schematic diagram showing the portable cytometer of FIG. 2 with the cover depressed.

FIG. 3 is a more detailed schematic diagram showing the portable cytometer of FIG. 2 with the cover 18 not yet depressed. FIG. 4 is a more detailed schematic diagram showing the portable cytometer of FIG. 2 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative example, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve may be an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate. Alternatively, each valve may be a similar to that described in co-pending U.S. patent application Ser. No. 1100.1174101, entitled "ELECTROSTATICALLY ACTUATED VALVE", which is incorporated herein by reference.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 may be filled before the removable cartridge 14 is shipped for use, while the blood reservoir 62 is filled from sample collector port 32. A blood sample may be provided to the sample collector port 32, and through capillary action, the blood sample may be drawn into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors may be thermal anemometer type flow sensors, and/or of the microbridge or microbrick type flow sensor. Microbridge flow sensors are described in, for example, U.S. Pat. Nos. 4,478,076, 4,478,077, 4,501,144, 4,651,564, 4,683,159, and 5,050,429, all of which are incorporated herein by reference. An output signal from each flow sensor 80, 100 and 102 is provided to controller or processor 40 via one or more electrical connection between the removable cartridge and the base.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If two much pressure builds up in the secondary pressure chambers, the corresponding vent valve 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another example, downstream valves 110 are opened by mechanical action when the cover is closed.

Figure 5:
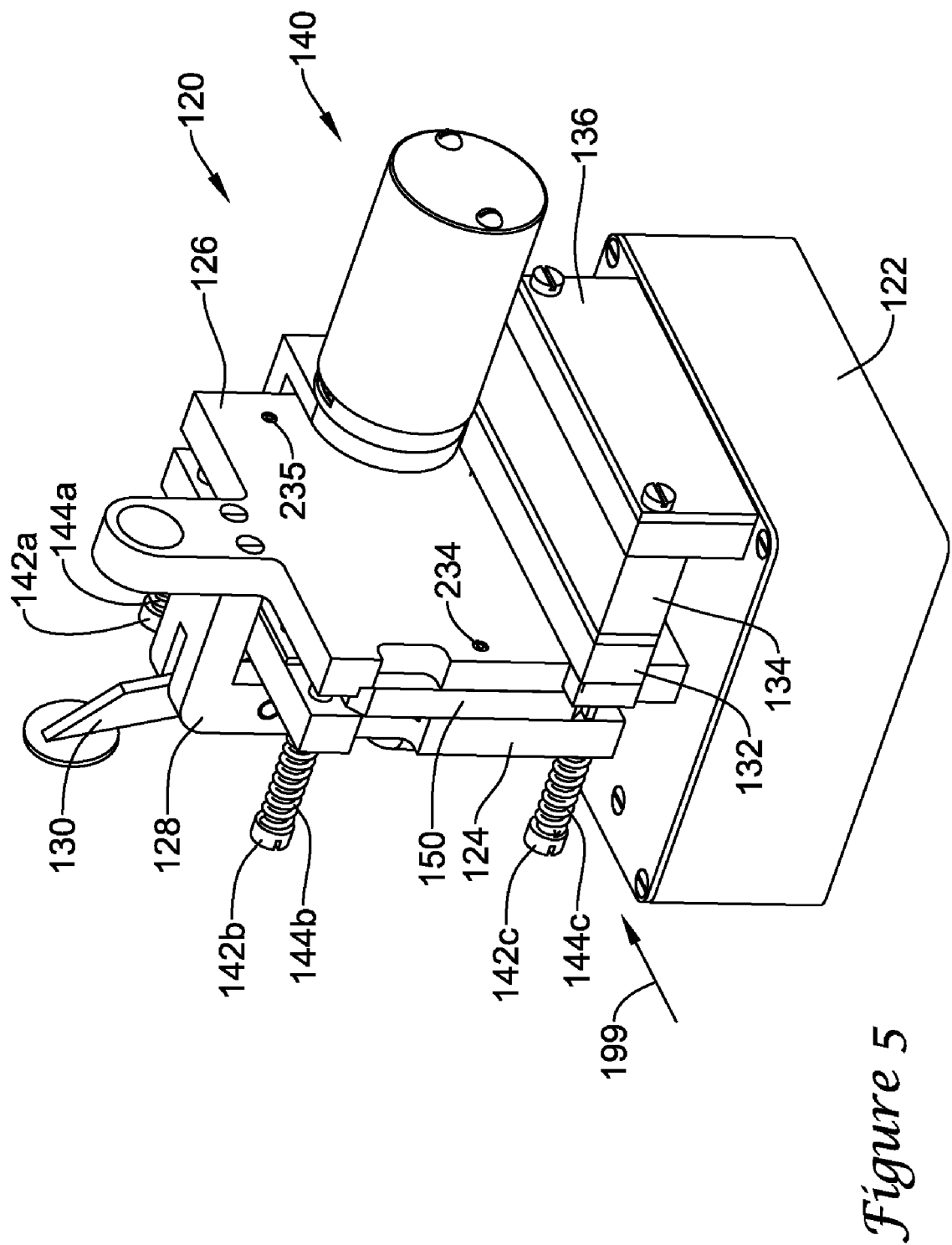
FIG. 5 is a perspective view of another illustrative portable cytometer.

FIG. 5 is a perspective view of another illustrative portable cytometer. The basic operation of the portable cytometer of FIG. 5 is similar to that described above with respect to FIGS. 1-4 above. The portable cytometer of FIG. 5 is generally shown at 120, and includes a base 122, a first member 124, a second member 126, a clamp frame 128 with clamp lever 130, an air buffer module 132, a valve module assembly 134 with polymer microvalves, an air accumulator module 136, and an optics assembly 140.

In the illustrative example, the second member 126 is fixed to the base 122. A number of shoulder screws 142a, 142b, 142c and 142d (142d not shown in FIG. 5) pass through holes in the first member 124 and are secured to the second member 126. Springs 144a, 144b, 144c and 144d (144d not shown in FIG. 5) are placed between the first member 124 and the head of the corresponding shoulder screw 142a, 142b, 142c and 142d. The springs 144a, 144b, 144c and 144d provide a bias force to the first member 124 toward the second member 126.

The clamp frame 128 is secured to the second member 126 as shown. The clamp lever 130 interacts with the clamp frame to provide an outward bias force to the first member away from the second member 126. By moving the clamp lever 130 in a first direction, the first member 124 is moved away from the second member 126 by overcoming the inward bias force provided of spring 144a, 144b, 144c and 144d. By moving the clamp lever 130 in a second opposite direction, the first member 124 is moved toward the second member 126, assisted by the inward bias force provided of spring 144a, 144b, 144c and 144d.

Figure 6:
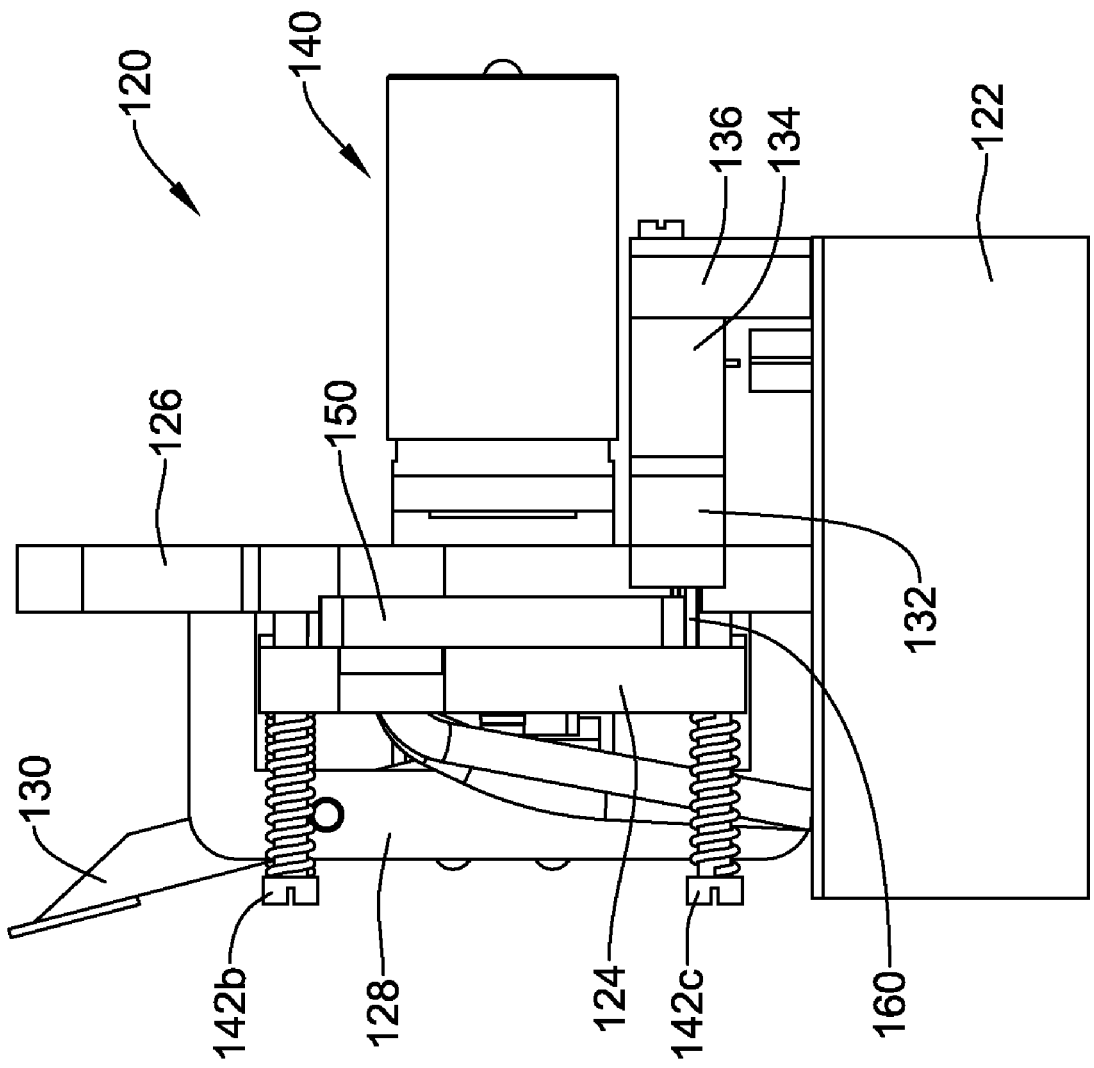
FIG. 6 is a perspective side view of the illustrative portable cytometer of FIG. 5.

During operation, the clamp lever 130 may be moved in the first direction to move the first member 124 away from the second member 126, leaving a space therebetween. A removable media member, such as a removable fluidic cartridge 150, may then be slid into the space. The removable cartridge 150 may have a front side, a back side, and one or more lateral sides extending between the front side and the back side, as shown. The clamp lever 130 may then be moved in the second direction to move the first member 124 toward the second member 136 to secure and/or engage the removable media member 150, as shown in FIG. 5. FIG. 6 is a perspective side view of the illustrative portable cytometer of FIG. 5.

In one illustrative example, the removable media member 150 has one or more fluid ports in the front and/or back sides, similar to that described above with respect to FIGS. 1-4. It is contemplated that the one or more fluid ports may be adapted to accept either a gas or a liquid, depending on the application. The second member 126 of the illustrative example includes corresponding fluid ports that align with the one or more fluid ports of the removable media member 150. One such fluid port is shown at 160 in FIG. 6. A fluid port gasket (see FIG. 12 below) may be secured to the second member 126 to help provide a better seal, if desired.

A fluid control module may then be fluidly coupled to the fluid ports of the second member 126. In the illustrative example, the fluid control module includes the air accumulator module 136, the valve module assembly 134 with polymer microvalves, and the air buffer module 132. The air accumulator module 136 includes an internal chamber for accumulating air pressure. A port (not shown) may be provided from the internal chamber of the air accumulator 136 to an air pressure source. The accumulated air pressure may be supplied to the valve module assembly 134. The valve module assembly may include one or more microvalves, such as polymer microvalves as disclosed in U.S. patent application Ser. No. 1100.1174101, entitled "ELECTROSTATICALLY ACTUATED VALVE", which is incorporated herein by reference. In the illustrative example, the valve module assembly 134 may provide three separate pressure channels including a blood channel, a lyse channel and a sheath channel, as shown and described above with respect to FIGS. 1-4. The valve module assembly 134 may be controlled by a controller in base 122 to provide three separate controlled pressures to air buffer module 132. Air buffer module 132 buffers the controlled pressures, and delivers the pressurized air to the fluid ports of the removable media member 150 via the fluid ports that pass in or through the second member 126.

In some cases, the removable media member 150 may include one or more electrical and/or optical devices. For example, and in the illustrative example, the removable media member 150 may include three flow sensors, with each flow sensor measuring the flow rate of the pressurized fluid through one of the three separate pressure channels of the removable media member 150. Like above, the flow sensors may be thermal anemometer type flow sensors, and/or of the microbridge or microbrick type flow sensor, commercially available from Honeywell International. Microbridge flow sensors are described in, for example, U.S. Pat. Nos. 4,478,076, 4,478,077, 4,501,144, 4,651,564, 4,683,159, and 5,050,429, all of which are incorporated herein by reference. An output signal from each flow sensor is provided to controller or processor in base 122, via an electrical and/or optical coupling between the removable media member and the second member 126.

The optical assembly module 140 may include one or more light sources (e.g. VCSELs) on one side of the removable cartridge 150, one or more light detectors on the opposite side of the removable cartridge 150, and associated optics. When so provided, the removable cartridge 150 may include a transparent flow stream window, which is in alignment with the one or more light sources and one or more light detectors. The air buffer module 132, valve module assembly 134, and air accumulator module 136 may be controlled to form a core stream down a flow stream path that passes the flow stream window in the removable cartridge 150. The light sources, when activated, provide light through the core stream via one side of the flow stream window. The optical detectors receive scattered and non-scattered light from the core stream via the opposite side of the flow stream window. A controller or processor in the base 122 then receives output signals from the detectors, and differentiates and counts selected white blood cells that are present in the core stream.

Figure 7:
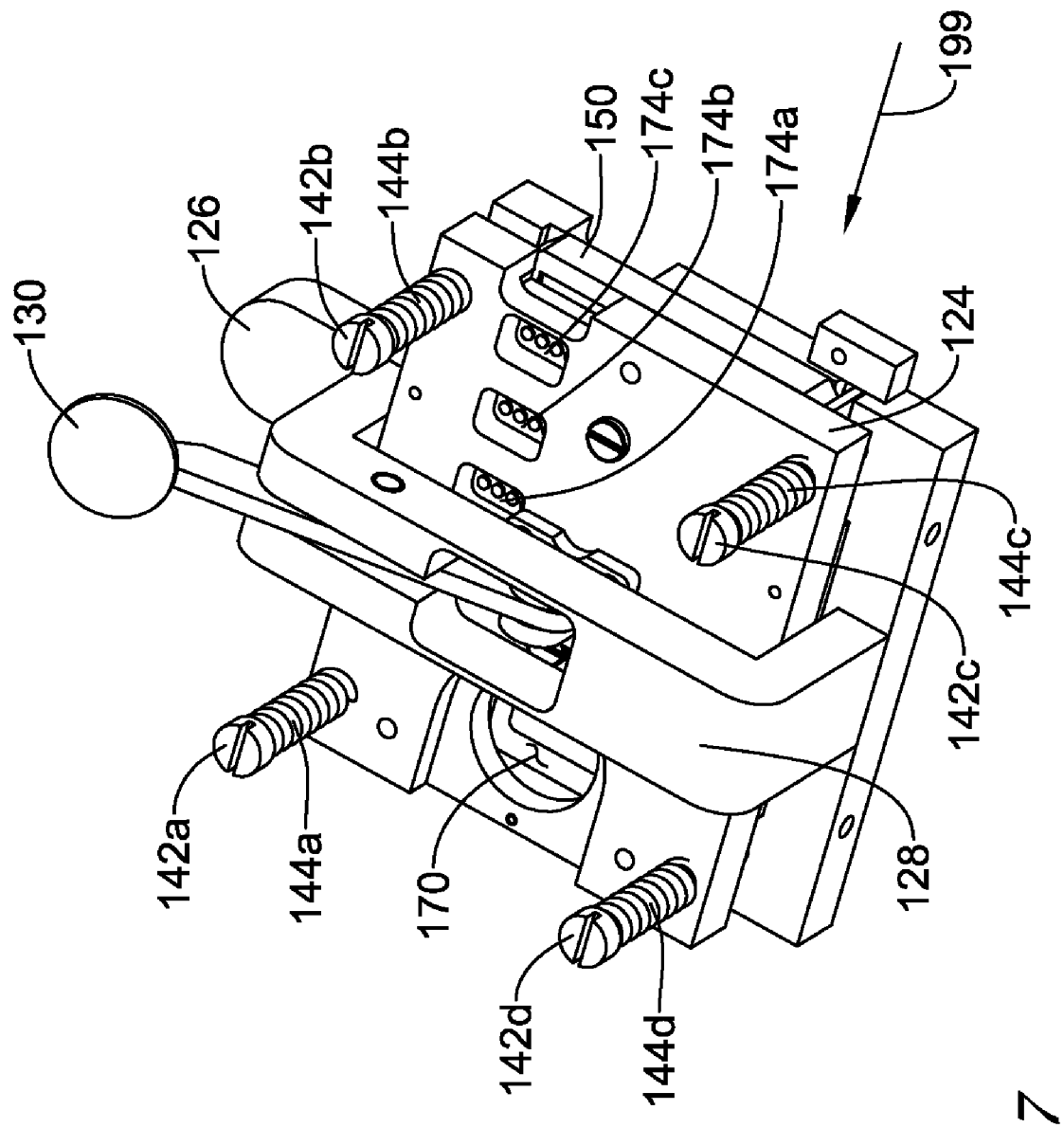
FIG. 7 is another perspective view of the illustrative portable cytometer of FIG. 5.

FIG. 7 is another perspective view of the illustrative portable cytometer of FIG. 5, further illustrating additional detail. FIG. 7 shows a hole 170 through the first member 124 and second member 126. The hole 170 may allow the one or more light sources and one or more light detectors of the optical assembly module 140 to directly access the flow stream window of the removable cartridge (not shown in FIG. 7).

FIG. 7 also shows one or more spring biased probes secured to the first member 124. The one or more spring biased probes may be positioned to align with the one or more electrical contact pads on the removable cartridge when the removable cartridge is at a desired positioned between the first member 124 and the second member 126. In the illustrative example, three arrays of spring biased probes 174a, 174b and 174c are provided, with each array mounted via a small PC board and secured within a corresponding hole in the first member 124. The holes in the first member 124 may provide access to the reverse side of the spring bias probes, which in some examples, may provide a convenient location to make an electrical connection between a controller in the base 122 and each spring bias probe.

In addition, or alternatively, it is contemplated that one or more optical transmitters and/or optical detectors may be secured to the first and/or second member. The one or more optical transmitters and/or optical detectors may be positioned to align with the one or more optical detectors and/or optical transmitters on the removable cartridge when the removable cartridge is at a desired positioned between the first member 124 and the second member 126. This may provide an optical link between the removable cartridge and the first member and/or second member 126, as desired.

Figure 8:
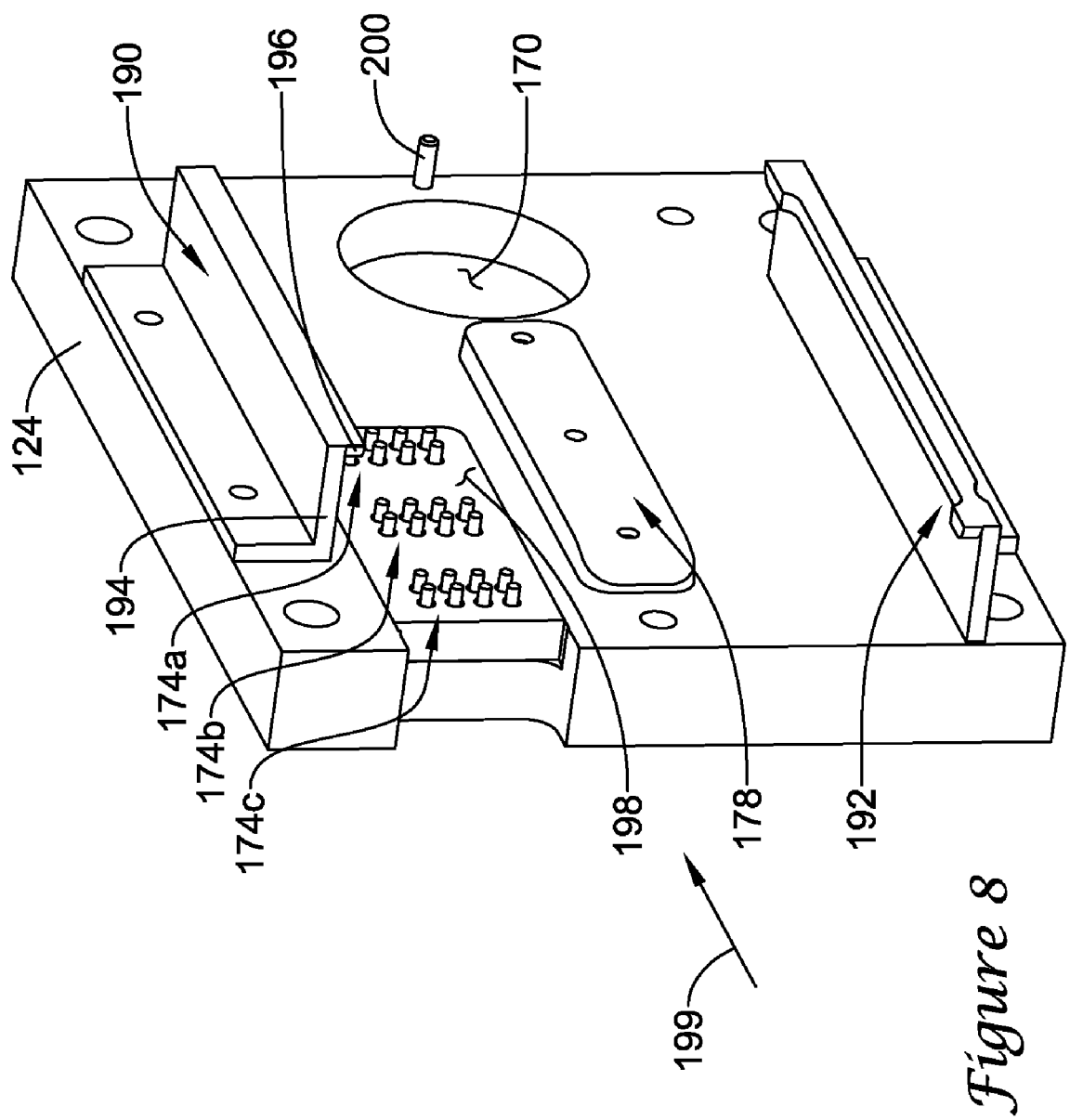
FIG. 8 is a perspective view of the first plate or member of the illustrative portable cytometer of FIG. 5.

FIG. 8 is a perspective view of the first member 124 of the illustrative portable cytometer of FIG. 5. FIG. 8 shows the opposite side of the three arrays of spring biased probes 174*a*, 174*b* and 174*c* of FIG. 7. As can be seen, each spring bias probes is biased by a spring in an outward direction away from the first member 124 and toward the removable cartridge (not shown in FIG. 8). The spring biased probes may be positioned to align with the one or more electrical contact pads on the removable cartridge when the removable cartridge is at a desired positioned between the first member 124 and the second member 126. When the first member 124 and the second member 126 are moved toward one another to secure and/or engage the removable cartridge, the spring biased probes may make electrical contact with the one or more electrical contact pads on the removable cartridge.

Figure 11:
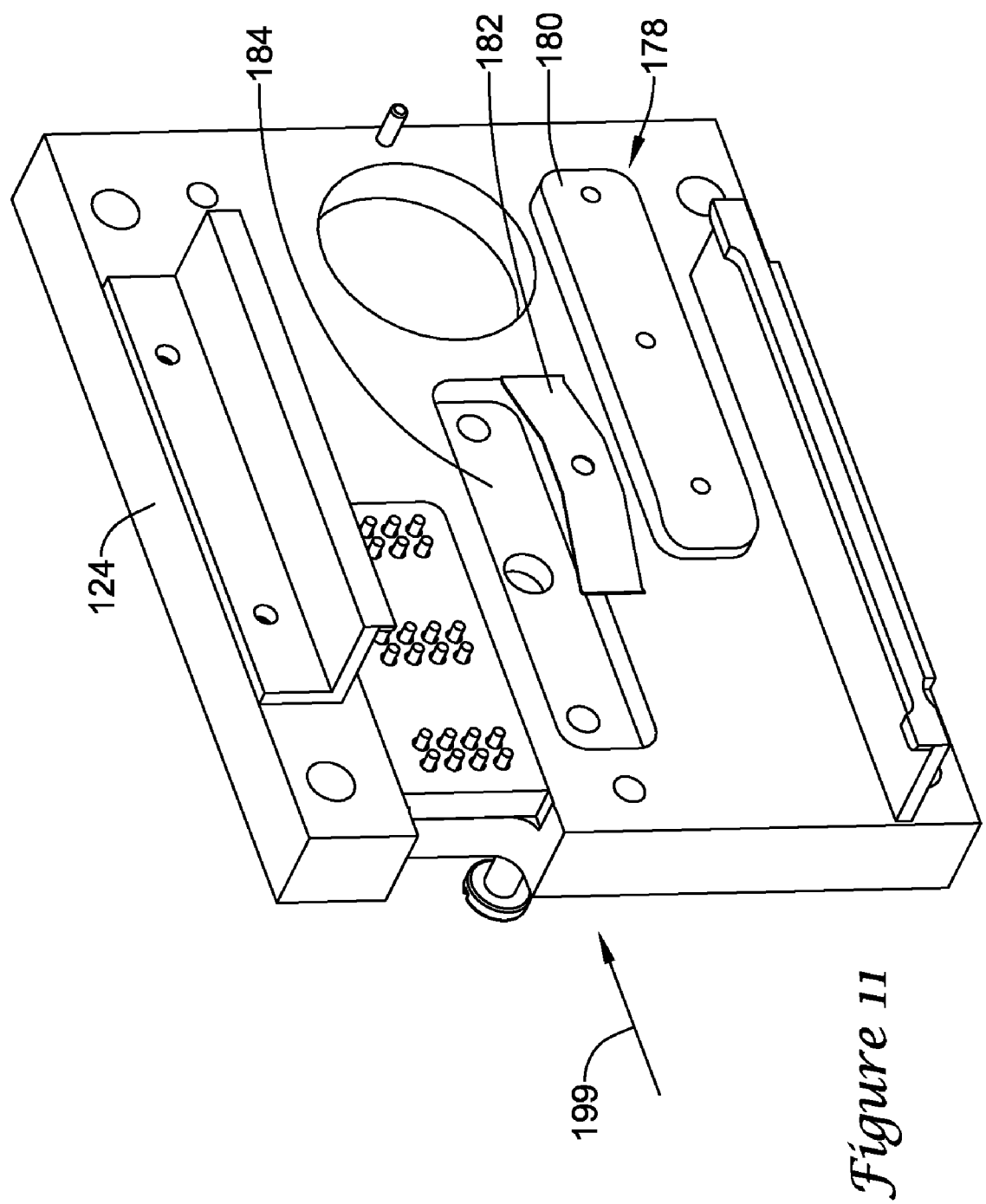
FIG. 11 is a perspective view of the outward bias wedge of the first plate or member of FIG. 8.

To help separate the spring biased probes from the one or more electrical contact pads on the removable cartridge when the first member 124 is moved away from the second member 126, an outward or separating bias 178 may be provided between the first member 124 and the removable cartridge. Referring momentarily to FIG. 11, the outward bias 178 may include a wedge 180 and a spring 182. The spring 182 may be positioned in a recess 184 in the first member 124, with the wedge 180 biased in an outward direction by the spring 182.

Referring back to FIG. 8, the outward bias 178 may be overcome when the first member 124 and the second member 126 are moved toward each other to secure and/or engage the removable cartridge. However, when the first member 124 and the second member 126 are moved away from each other to release the removable cartridge, the outward bias 178 may separate the one or more spring biased probes 174*a*, 174*b* and 174*c* from the one or more electrical contact pads of the removable cartridge, which may make the removal of the removable cartridge from between the first member 124 and the second member 126 easier and may help protect the spring bias probes from damage during the removal process.

The first member 124 may also have one or more L-shaped cleats that provide a slot to receive the removable cartridge. In the illustrative example of FIG. 8, an upper L-shaped cleat 190 and a lower L-shaped cleat 192 are provided. The L-shaped cleats 190 and 192 may each include, for example, a first leg 194 that extends away from the first member 124 and toward the second member, and a second leg 196 that extends from a distal end of the first leg 194 and in a perpendicular direction relative to the first leg 194 so that a channel or receiving slot 198 is formed. The channel or receiving slot 198 may then receive one side of the removable media member. In the illustrative example, the upper L-shaped cleat 190 includes a second leg 196 that extends in a downward direction, and the lower L-shaped cleat 192 includes a second leg that extends in an upward direction. In addition, the upper L-shaped cleat 190 and the lower L-shaped cleat 192 are spaced so that two spaced channels 196 are provided for receiving opposing sides (e.g. upper side and lower side) of the removable cartridge. That is, the channel or slot of the upper L-shaped cleat 190 and the channel or slot of the lower L-shaped cleat 192 are arranged so that the removable cartridge slides into both channels when it is inserted between the first member 124 and the second member 126. In the illustrative example, the two L-shaped cleats are secured to the first member 124.

An alignment pin 200 may be provided toward the back of the first member 124 to engage the back of the removable cartridge. The alignment pin 200 may be positioned to stop the removable cartridge at or near the desired insertion position between the first member 124 and the second member 126.

During use, the first member 124 and the second member 126 may be moved away from one another, and the removable cartridge may be slid into the channel or receiving slots 198 provided by the L-shaped cleats 190 and 192 until the removable cartridge engages the alignment pin 200. The L-shaped cleats 190 and 192 may be positioned so that that when the removable cartridge is received by the L-shaped cleats 190 and 192, the removable cartridge is at least roughly aligned with a desired position relative to the first member 124 and/or second member 126. The first member 124 and the second member 126 may then be moved toward one another to engage and/or secure the removable cartridge therebetween.

To remove the removable cartridge, the first member 124 and the second member 126 may be moved away from each other. Because the upper and lower edges of the removable cartridge are positioned in the channel or slot 198 of the L-shaped cleats 190 and 192, the removable cartridge is pulled away from the second member 126 by the second legs 196 of the L-shaped cleats 190 and 192 as the first member 124 and second member 126 are moved away from each other.

Figure 12:
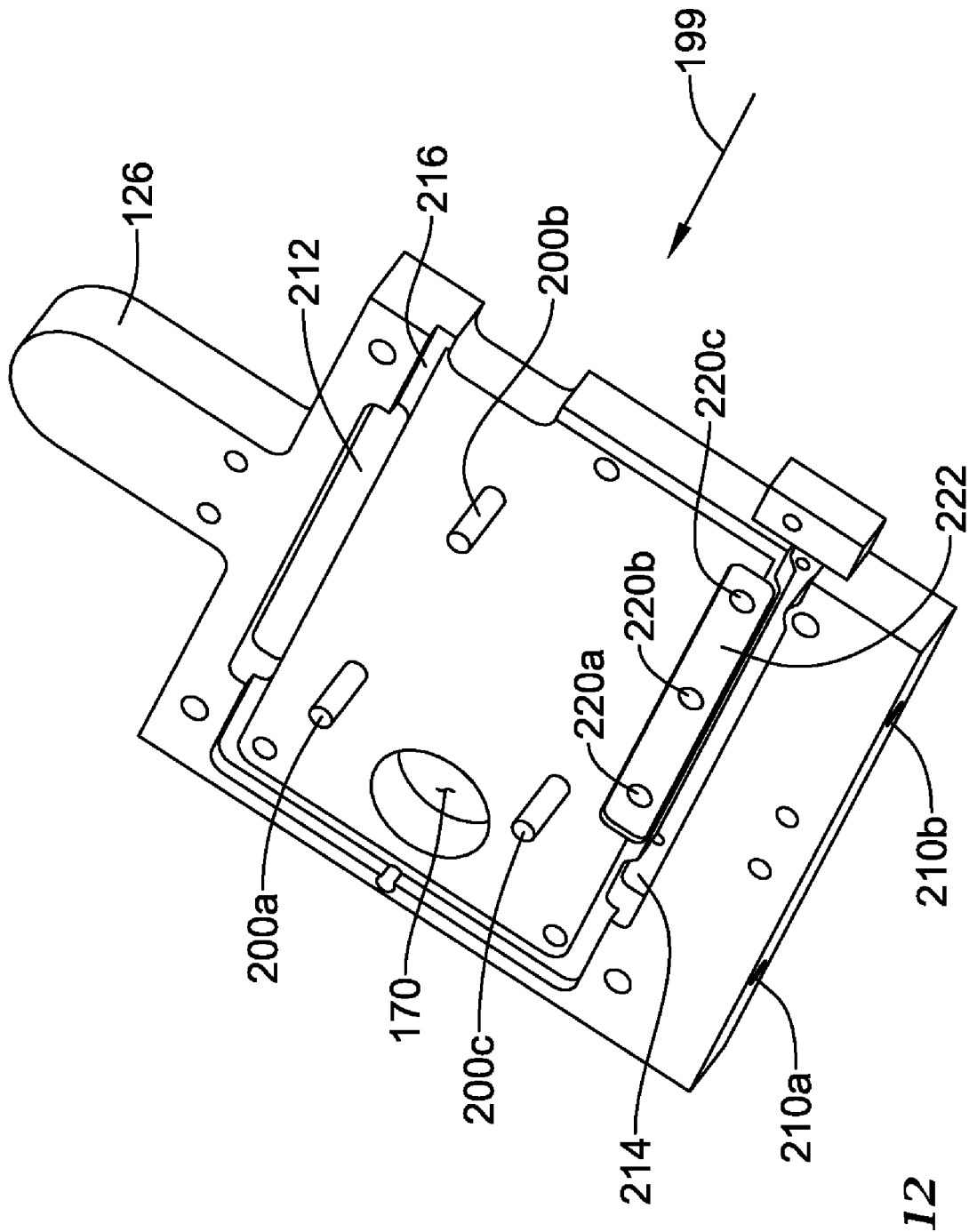
FIG. 12 is a perspective view of the second plate or member of the illustrative portable cytometer of FIG. 5.

To provide better alignment between the removable media member and the first member 124 and/or the second members 126, the second member 126 may include one or more alignment pins 200*a*-200*c* that extend toward the first member (see FIG. 12). The removable media member 150 may then include one or more receiving holes for receiving the one or more alignment pins 200*a*-200*c*. The alignment pins 200*a*-200*c* and receiving holes may provide improved alignment between the removable media member 150 and the first member 124 and/or second member 126 when the removable media member 150 is secured between the first member 124 and the second member 126.

The L-shaped cleats 190 and 192 may be used to pull the removable media member 150 away from the second member 126, thereby separating the one or more receiving holes of the removable media member 150 from the one or more alignment pins 200*a*-200*c* that are extending from the second member 126. With the one or more receiving holes separated from the alignment pins 200*a*-200*c*, the removable media member 150 then may be more easily removed from between the first member 124 and the second member 126.

FIG. 9 is a perspective view of the lower cleat 192 of FIG. 8. The illustrative lower cleat 192 includes a first leg 194*a* and a second leg 196*a*, wherein the second leg 196*a* extends from a distal end of the first leg 194*a* and in a perpendicular direction to form a channel or receiving slot 198*a*. A mounting leg 202*a* may extend from the first leg 194 as shown, for mounting the lower cleat 192 to the first member 124.

FIG. 10 is a perspective view of the upper cleat 190 of FIG. 8. The illustrative upper cleat 190 includes a first leg 194*b* and a second leg 196*b*, wherein the second leg 196*b* extends from a distal end of the first leg 194*b* and in a perpendicular direction to form a channel or receiving slot 198*b*. A mounting leg 202*b* may extend from the first leg 194*b* as shown, for mounting the upper cleat 190 to the first member 124.

FIG. 12 is a perspective view of the second plate or member 126 of the illustrative portable cytometer of FIG. 5.

The second member 126 may be fixed to the base 122 by screws that are threaded into screw holes 210a and 210b. As detailed above, the second member 126 may further include a hole 170 that may allow the one or more light sources and one or more light detectors of the optical assembly module 140 to directly access the flow stream window of the removable cartridge.

In the illustrative example, the second member 126 includes a flat major surface with a recessed portion for receiving the removable cartridge. To provide better alignment between the removable cartridge and the first member 124 and/or the second members 126, the second member 126 may include one or more alignment pins 200a-200c that extend toward the first member. The removable cartridge 150 may then include one or more receiving holes for receiving the one or more alignment pins 200a-200c. The alignment pins 200a-200c and receiving holes may provide improved alignment between the removable cartridge and the first member 124 and/or second member 126 when the removable cartridge is secured between the first member 124 and the second member 126.

Additional recesses 212 and 214 may be included to receive the second legs 196a and 196b of the upper L-shaped cleat 190 and lower L-shaped cleat 192, respectively (see FIGS. 8-10). By providing relief for the second legs 196a and 196b of the upper L-shaped cleat 190 and lower L-shaped cleat 192, the removable cartridge may directly engage the surface of the second member 126.

In some cases, the manufacture of the removable cartridge may create a ridge, a burr, or other imperfections, particularly around the outer perimeter of the removable cartridge. In one example, a fluidic cartridge may be manufactured by laminating several layers or sheets together, and then cutting individual fluidic cartridges from the laminated structure. At the cut lines, ridges, burrs, and/or other imperfections may arise. To help the removable cartridge seat flush with the surface of second member 126, a groove 216 or other relief structure may be provided in the receiving surface of the second member 126 to accommodate the one or more imperfections in the removable cartridge. In the illustrative example of FIG. 12, a groove 216 may extend along a groove path that extends around the perimeter of the removable cartridge. It is contemplated, however, that a groove or other relief structure may be provided at any location where an anticipated imperfection might occur in the removable cartridge. It is also contemplated that a groove or other relief structure may be provided in the receiving surface of the first member 124, if desired.

In one illustrative example, the removable cartridge has one or more fluid ports, similar to that described above with respect to FIGS. 1-4. It is contemplated that the one or more fluid ports may be adapted to accept either a gas or a liquid, depending on the application. The second member 126 of the illustrative example includes corresponding fluid ports 220a-220c that align with the one or more fluid ports of the removable cartridge. A fluid port gasket 222 may be secured to the second member 126 to help provide a better seal, if desired.

Figure 13:
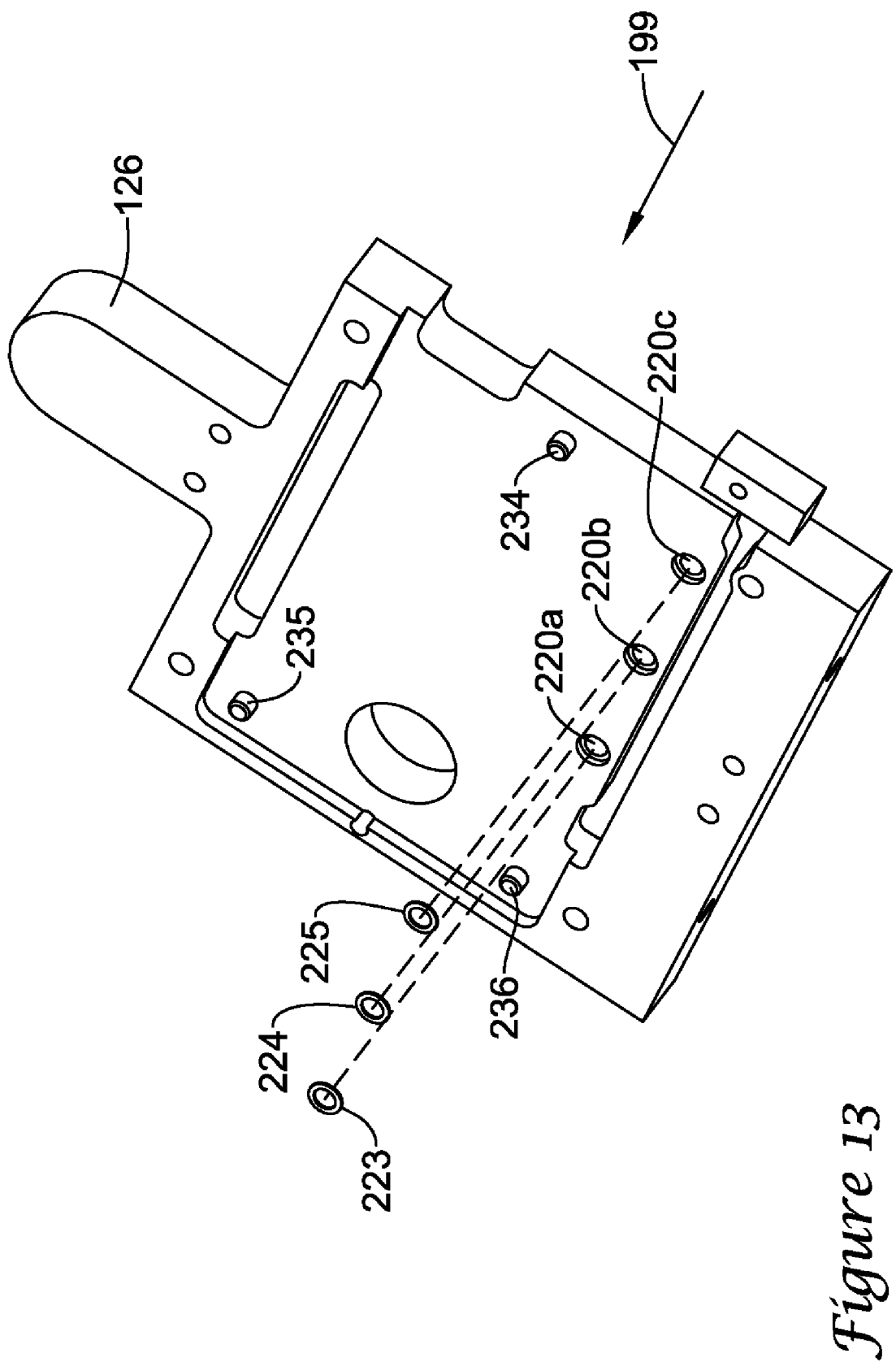
FIG. 13 is a perspective of a modified second plate of member of the illustrative cytometer.

FIG. 13 is a perspective view of the second member 126 with the single gasket 222 of FIG. 12. This single gasket may have been fraught with difficulties such as leaks. A cure against leaks at the interface having the single piece gasket 222 may have included a thicker tape under the gasket and more clamp pressure from the first element 124 on the cartridge 150 to push the cartridge with greater force against the second element 126. Gasket 222 may be removed and replaced with three separate gaskets 223, 224 and 225, for the ports 220a, 220b and 220c for the movement of the sheath fluid, the lyse and the sample, respectively, from second member 126 to the cartridge 150 at its input ports 231, 232 and 233. The gaskets may be O-ring shaped and made from a silicone or like material. The replacement of gasket 222 with the individual gaskets 223, 224 and 225 may provide much greater assurance for prevention of leaks at those fluidic connections between the cartridge 150 and the second member 126. In view of FIG. 6, insufficient clamp pressure of first member 124 against the cartridge 150 towards the second member 126 may affect the integrity of the seals at the interface of the two sets of ports, particularly without the individual gaskets. Leaks at this interface not only may result in fluid coming out of the system but allow air to enter the fluidic network or circuit.

For easier insertion of cartridge 150 and accurate alignment of the cartridge with the second member 126, alignment pins 234, 235 and 236 may be shorter (FIG. 13) than the original pins and replace the one or more original alignment pins 200a, 200b and 200c (FIG. 12). The key alignment may be provided by pin 234 of the second member 126 relative to hole 237 of card 150. The other pins 235 and 236 may be present to prevent swinging of the cartridge about the pivot guide pine 234. More or less alignment pins may instead be present in the second member 126. Alignment pins 234, 235 and 236 may fit into alignment holes 237, 238 and 239, respectively.

Flow sensors 226, 227 and 228 may be situated in cartridge 150 and may be connected via three arrays of spring biased probes 174a, 174b and 174c, respectively, on the first member 124 to electronics situated off the cartridge. The flow sensors 226, 227 and 228 may be utilized for the monitoring the flow of the sheath fluid, the lyse and the sample, respectively. The flow sensors may be placed in the cartridge in an area 240 of FIG. 14a. The flow sensors 226, 227 and 228 may be countersunk into the cartridge with their electrical contacts facing away from the cartridge so that when cartridge 150 is inserted in the direction 199 in the slot between members 124 and 126, from left to right in FIG. 7, such that the contacts of the flow sensors line up with the arrays of the spring based probes 174a-174c, in the upper right portion 240 (FIG. 14a), so as to make an appropriate electrical contact with them. Between the flow sensors and a surface of the cartridge to make connection with fluid ports communication with the sheath fluid, lyse and the sample, there may be a tape and/or adhesive on the surface with holes to the ports to seal the flow sensor and prevent leakage of the sheath, lyse and/or sample from the fluidic connections between the flow sensors and the cartridge. To better insure against leakage, the tape and/or adhesive may be replaced or overlaid with a gasket of similar shape having three holes lining up with the ports. The gasket may be a custom molded gasket for the interface between the flow sensors and the cartridge. Or the interface may incorporate separate O-ring-like gaskets or seals. An adhesive on the flow channel at the top of the respective sensor may be used along with the custom gasket to ease the interchangeability and reusability of the flow sensors from one cartridge to another. The flow sensors may be insertable and removable relative to the cartridge. Once a cartridge is used and becomes disposable, the flow sensors may be removed, cleaned and inserted into a new cartridge to be used for testing and analysis of a sample. Inexpensive flow sensors may be placed in the cartridge in a more permanent manner and be disposed along with the cartridge after completion of the usage. The flow sensor gasket placed in the cartridge may facilitate the moving of the flow sensors from cartridge to cartridge without the risk of leakage.

The cartridge 150 may be fabricated from a plastic or a plastic-like material. Some portions of the walls are thicker for structural rigidity and other portions are thinner so as to provide space in the cartridge for storage of fluids, microfluidic channels and mechanisms. Also, the portion with the fluid flow channel has thin walls to provide a narrow channel for single file flow of the particles in a core stream and to adequately support the light source and detector optics for correct focusing and observation of the core stream in the flow channel. Thin walls may be situated where the various fluid reservoirs and mixing channels are located in the cartridge.

Figure 14A:
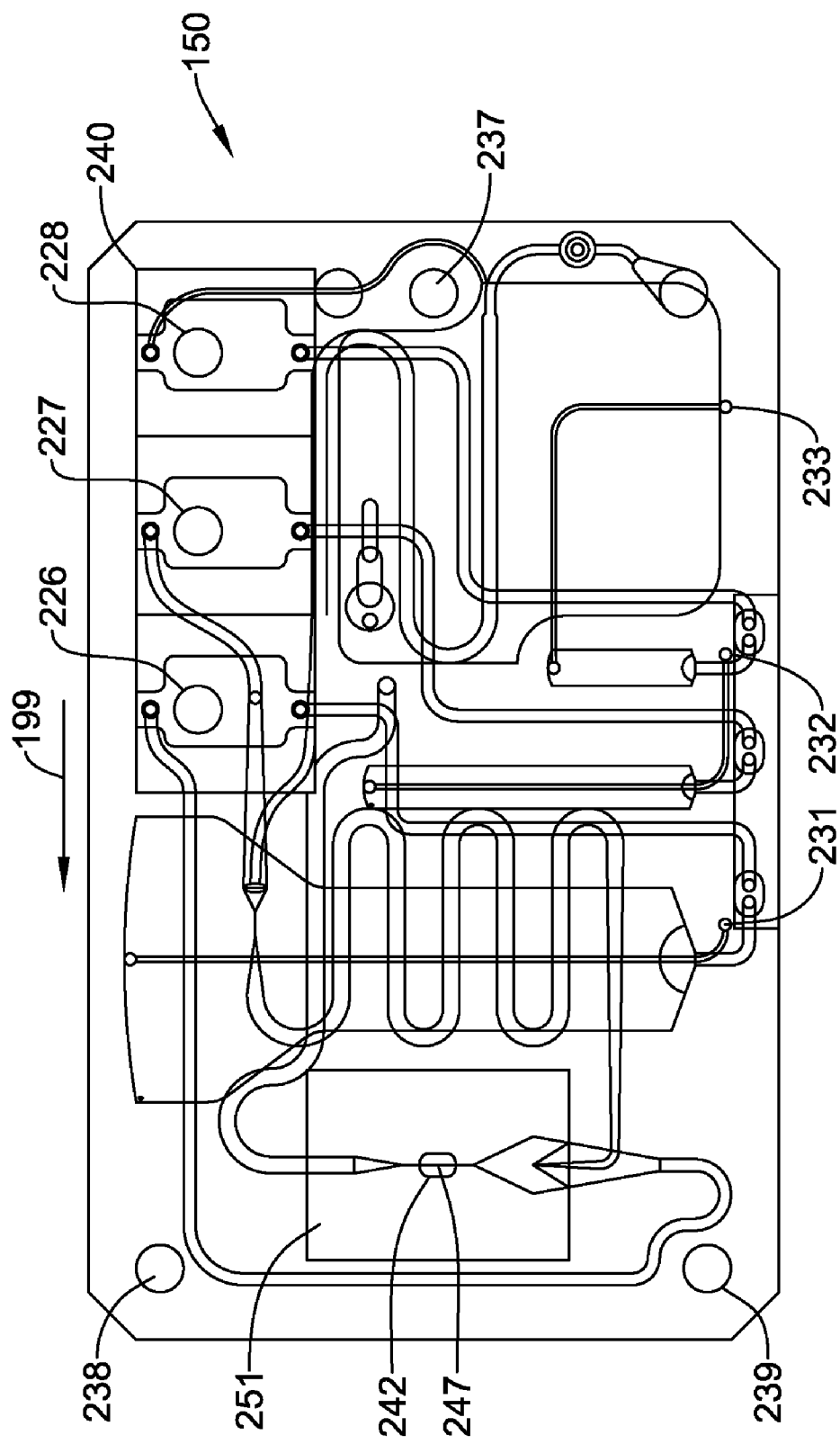
FIG. 14a is a plan view of an insertable cartridge.
Figure 14B:
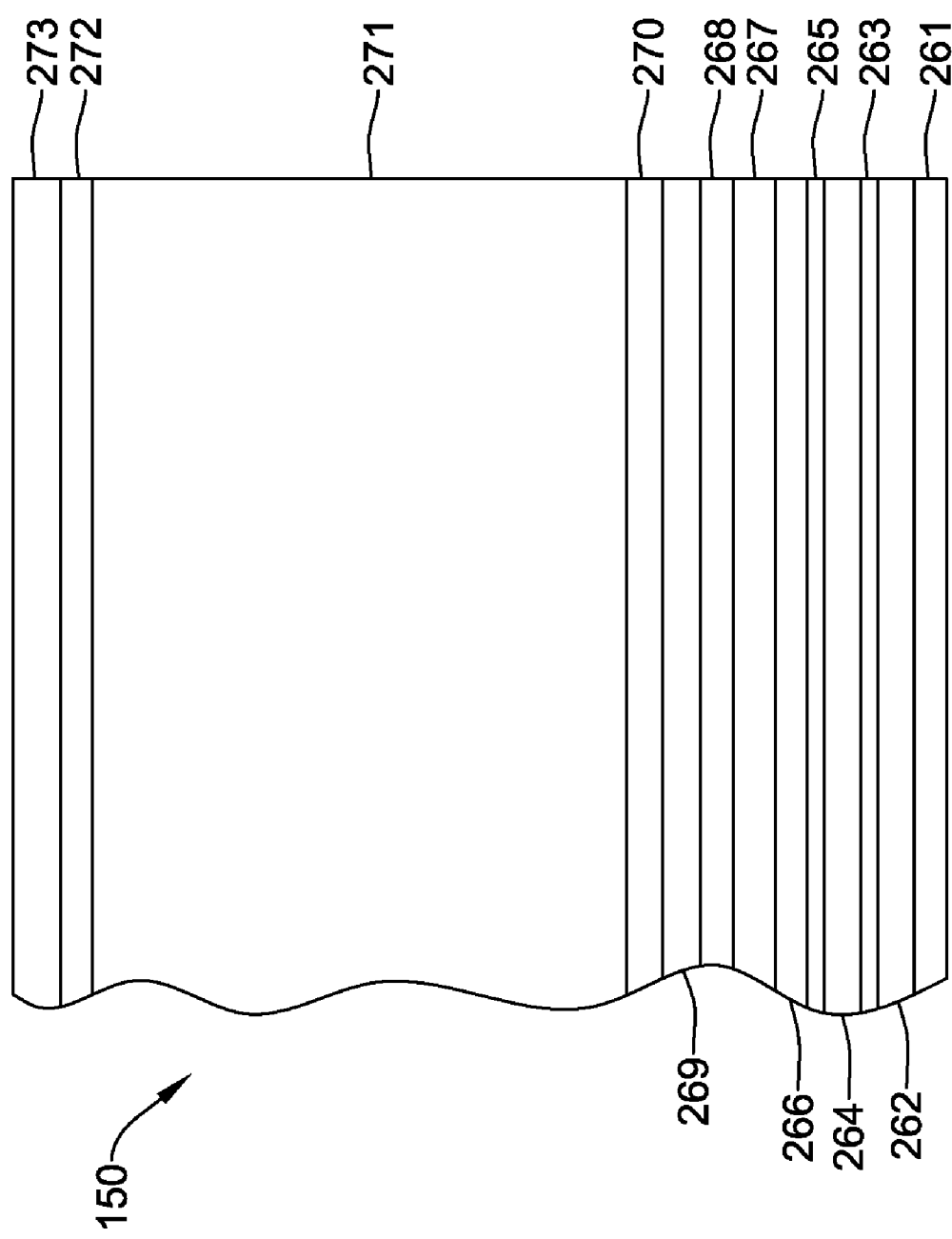
FIG. 14b is an edge view of the cartridge.

An illustrative layer arrangement of cartridge 150, from the bottom up as cartridge 150 is positioned in FIG. 14a with the flow channel 247 to the left at the bottom side, and with an edge view of the cartridge 150 in FIG. 14b, may include: layer 261—PET—5 mils normal; layer 262—ACA—6 mils normal; layer 263—PET—2 mils normal; layer 264—ACA—4 mils normal; layer 265—PET—2 mils inverted; layer 266—ACA—6 mils normal; layer 267—PET—5 mils inverted; layer 268—ACA—4 mils normal; layer 269—PET—5 mils inverted; layer 270—ACA—6 mils normal; layer 271—acrylic—125 mils normal; layer 272—ACA—6 mils normal; and layer 273—PET—5 mils normal. There may be more or less layers sometimes depending on the desired specifications and application of card 150. The Figures are not necessarily to scale.

The thin layers may be of a very precisely controlled thickness. Again, the cytometer flow channel, mixing channels, sample storage, serpentine channels (such as those for mixing lyse and blood), and other items of critical dimensions may be located in these layers. The walls of the storage should be adequate to ensure compliance of the storage. The thick layer is of less precise thickness. The reagent storage and waste reservoirs are located in this layer. The thick layer provides the mechanical stiffness to the cartridge. The thin precise layers may "interface" with the cartridge clamp frame in such a manner to provide precise alignment of the cartridge relative to the optical subsystem incorporating the light source and detection arrangement. The precision thickness film may be made so as to control the spacing between the sample flow and the light source to ensure appropriate focusing. The thin precise layers may have a very carefully controlled thickness with possibly a less than four percent variation of the thickness. Thickness variation may be more critical in the optical area of the flow channel than other areas of the cartridge.

Figure 14C:
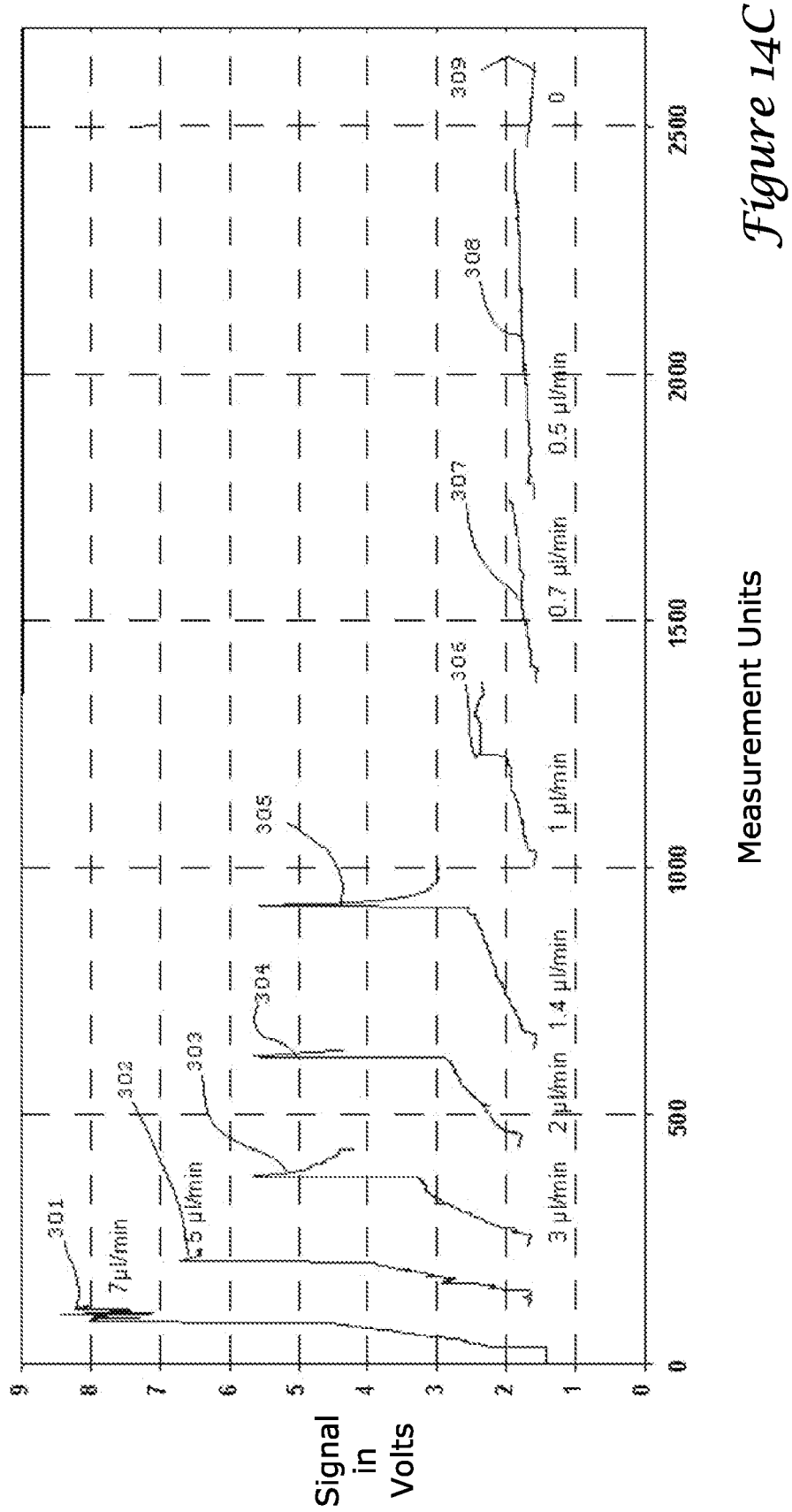
FIG. 14c is a graph of a cartridge flow test.
Figure 14D:
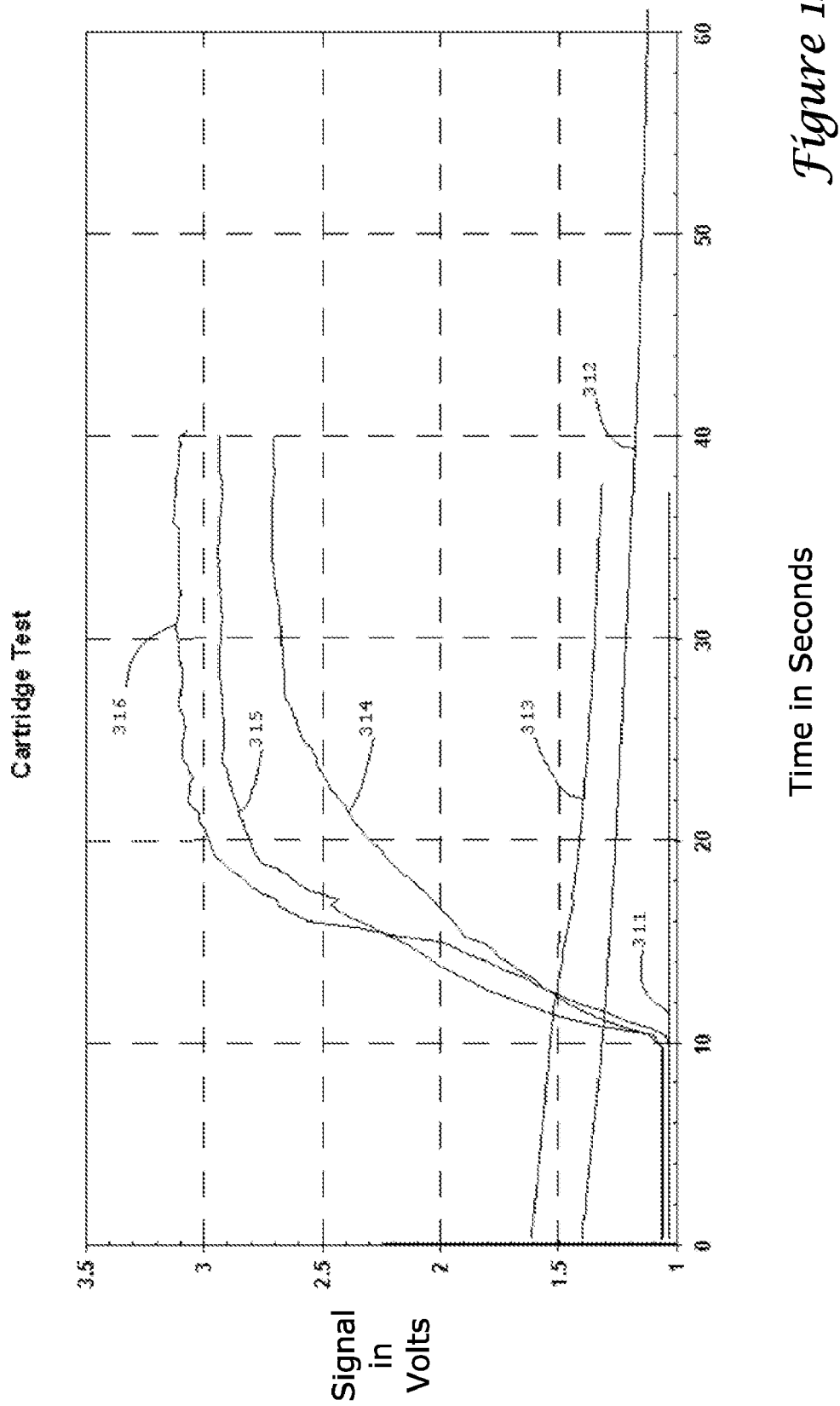
FIG. 14d is a graph of a cartridge test of flow rise and decay signals.

The thin walls may at times present observable phenomena relative to the cartridge, where there is a slow flow rise and decay with starting and stopping of a flow. Effects of those phenomena may be noted in graphed checks of a cartridge. FIG. 14c shows a sample flow signal of the cartridge having a removable embedded flow sensor. The graph reveals plot in terms of signal in volts versus measurement units. Curves 301, 302, 303, 304, 305, 306, 307, 308 and 309 indicated 7 micro liters per minute (um/min), 5 um/min, 3 um/min, 1.4 um/min, 1 um/min, 0.7 um/min, 0.5 um/min and 0 um/min, respectively. The high signal volts versus a small number of measurement units reveal a good star-up and the converse reveals a slow start-up which may be due to wall flexing and/or air in the system. FIG. 14d reveals sheath flow rise and zero flow decay signals for the cartridge. The measurements are signal in volts versus time in seconds. Plots 311, 312 and 313 represent zero A, zero F and zero D data, respectively. Plots 314, 315 and 316 represent 300 E, 500 C and 700 B data, respectively.

Flexing may affect the focus of the optics relative to the flow channel and problematic data taking. Also, thin walls may affect the pumping and the flow of the fluids in the microfluidic circuits thereby affecting the data taking. One reason is the reservoir walls may flex or have a concave or convex shape relative to the other portions of the cartridge. For instance, the surface of the reagent reservoir may be concave on some of the cartridges. That may prevent the surface touching the manifold surface of the cartridge holder when clamped, and thereby permits the thin wall to flex during operation of the fluidic elements in the cartridge. On the other hand, the thin wall surface is convex, particularly if the reservoir is filled, though it may remain convex when the reservoir is empty. Or the wall of a reservoir may be concave when the reservoir is sort of empty and convex when it is rather full. That means when a flow such as a sheath fluid flow is shut off there may be a slow change of pressure or a remnant of fluid that continues to flow. When the flow is turned on, there may be a delay of the starting of the fluid flow or a build up to operating pressure. These delays of fluidic action may be due to the contraction and expansion of the reservoir volume, respectively due the flexing of the thin walls. Sheath fluid control may be very critical and significantly affected by flexing thin walls. The change of sheath fluid flow may affect the width and speed of the core stream in the flow channel and lead to inaccurate or unreliable data accession by the cytometer detection system. Flexing of the thin walls may lead to air bubbles entering the system thereby affecting proper operation of the microfluidics of the cartridge, since air in the fluidic network may resulting in notable expansion and contraction with changes in pressure and/or temperature. There should be no flow when the sheath fluid is shut off. The start of the flow and/or pressure should be almost immediate when the flow is turned on. Without good starts and stops of the fluid, data taking may not be as reliable. When the cartridge is clamped, there may be backflow at a vent hole at the filter near the edge of the cartridge above the sample inlet. That may be because a check valve, if there is any, did not work to stop the backflow.

The thin walls may be reinforced with ridges. Ridges or beam-like structures may be also added along one of the dimensions (e.g., the lengthwise dimension) on the thin walls. Or these walls may be made thicker. These walls may consist of thin film material or materials. Additional films may stiffen the thin wall with a minimal thickness increase without compromising the small variation in thickness of the thin wall. Ridges or beam-like structures may also be added to further reinforce the thickened thin walls. Care should be taken because thickened and/or ridge-reinforced walls may prevent adequate clearance for the fluid and/or result in an air bubble trap. Also, the areas of thin walls on the cartridge may be made smaller or minimized where practical along with achieving the ensured performance expected of the components affected by conditions of the thin walls.

The reagent reservoirs of the cartridge originally had small holes at the top of them, one hole for each, for the independent filling them. However, there occasionally appeared to be an issue with bubbles entering the reagent reservoirs and a subsequent introduction of "compliance" in the fluidic network. For instance, when the reservoir was filled, it may be difficult to be sure that it was filled up to the top of the hole when closing, sealing or plugging the hole without any air being trapped in at the fill hole. For example, sealing a reagent reservoir fill hole may often inject an air bubble into the reservoir. The reservoirs may instead be filled thought the input ports to eliminate the issue. The small holes may be permanently plugged. The input ports would be used anyway for flow purposes. It may be noted that positive pressure in the cartridge after flow testing is stopped may force air bubbles back to the large reservoir. The pressure in the reservoir forced a backflow which returned the air to the reservoir. The disposable cartridges may have prepackaged fluids put on the cartridges during assembly.

As to the waste reservoir, the porous vent membrane may be moved further from the inlet since the entry of water would tend to seal the vent. The vent may be better moved to the opposite side of the reservoir without the membrane. However, for the finished cartridge the membrane or something like it may be used in the new vent location. The old vent may be intentionally plugged.

The cartridge may have three bellows valves that may be activated with a single lever on the edge of the cartridge. However, the valves may be individually activated to aid in filling. The reservoirs may be bench filled with a Harvard syringe pump. There may be fluid creep between the reservoirs when moving between reservoirs which could be due to a flexible surface of the reservoir wall. Individually activated valves that could be closed after a reservoir is filled may alleviate this problem. The volume of the large reservoir is not the same among the cartridges which may be due to reservoir compliance. Increased wall thickness may solve this issue, although it might have an effect on the optics referencing. There may be a concern relative to making electrical contact to the sensor since it would be recessed deep into the cartridge.

Figure 16:
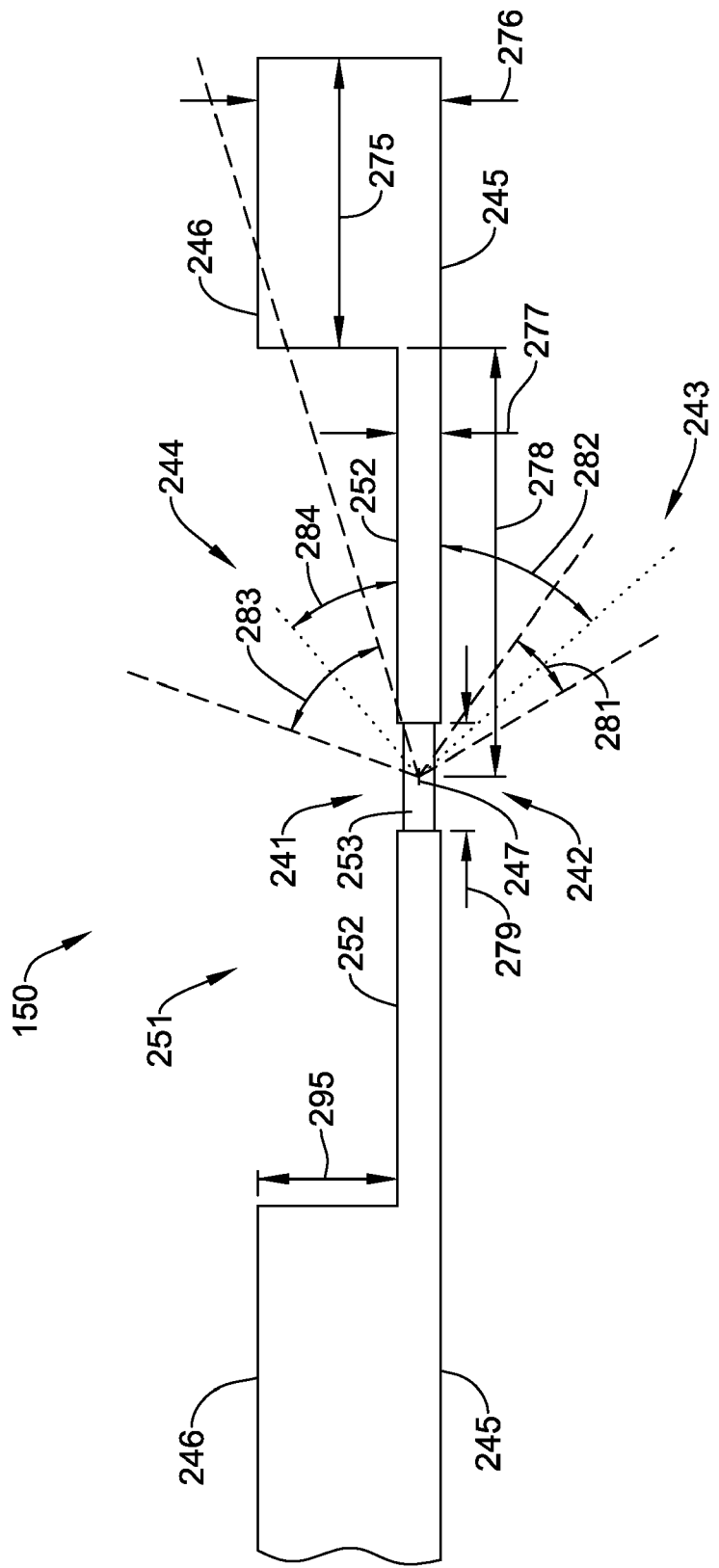
FIG. 16 shows a cross-section view of the top side of the cartridge showing a detector cone and a source cone relative to the flow channel window.

Cartridge 151 may be modified to accommodate advanced optics for the cytometer system. There are several approaches that may be achieved. FIG. 16 shows a cross-section view of the top side of the cartridge 150 showing a detector cone 244 and a source cone 243 relative to the flow channel windows 241 and 242, respectively. A counter-sunk opening 251 on the detector side may be sunk below the broad surface 246 of the cartridge 150 where a flow channel 247 is situated within thin layers 253 close to the general surface 245 opposite of surface 246 and close to a top surface 252 of opening 251. The source cone 243 may have an angle 281 of about a 20 degree wide spread. In other embodiments, the source cone 243 may have an angle that ranges up to 50 degrees. The direction of the light source cone 243 to the flow channel 247 may be at an angle 282 of about 45 degrees relative to the surface 245. There appears to be no interference of the cartridge window 242 relative to cone 243 since the window may be rather close to the surface 245. The flow channel 247 may contain a core stream that flows upwards out of the sheet containing the FIG. 16. Alternatively, the core stream may instead flow downward into the sheet of the figure; however, there might be a greater probability of air being taken into the core stream. The source cone and the detector cone are set at an angle relative to the window surface or flow channel of the cartridge so that there is not a line-of-sight or direct impingement of the source light through the flow channel to the detector. Nominally, the directions of the source and detector cones may be at about 90 degrees relative to each other.

Figure 15A:
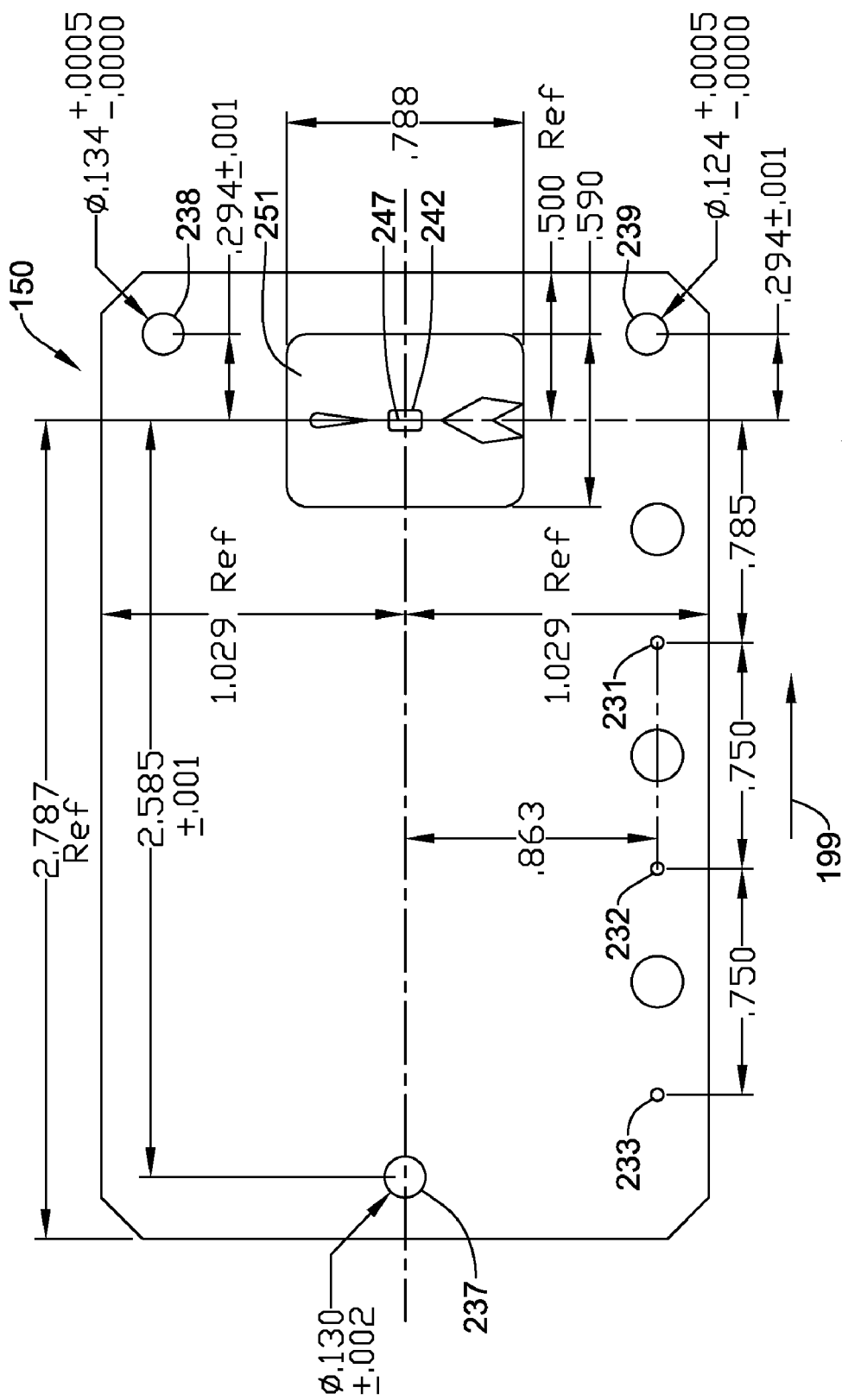
FIG. 15a is a plan view of the cartridge having several dimensions.
Figure 15B:
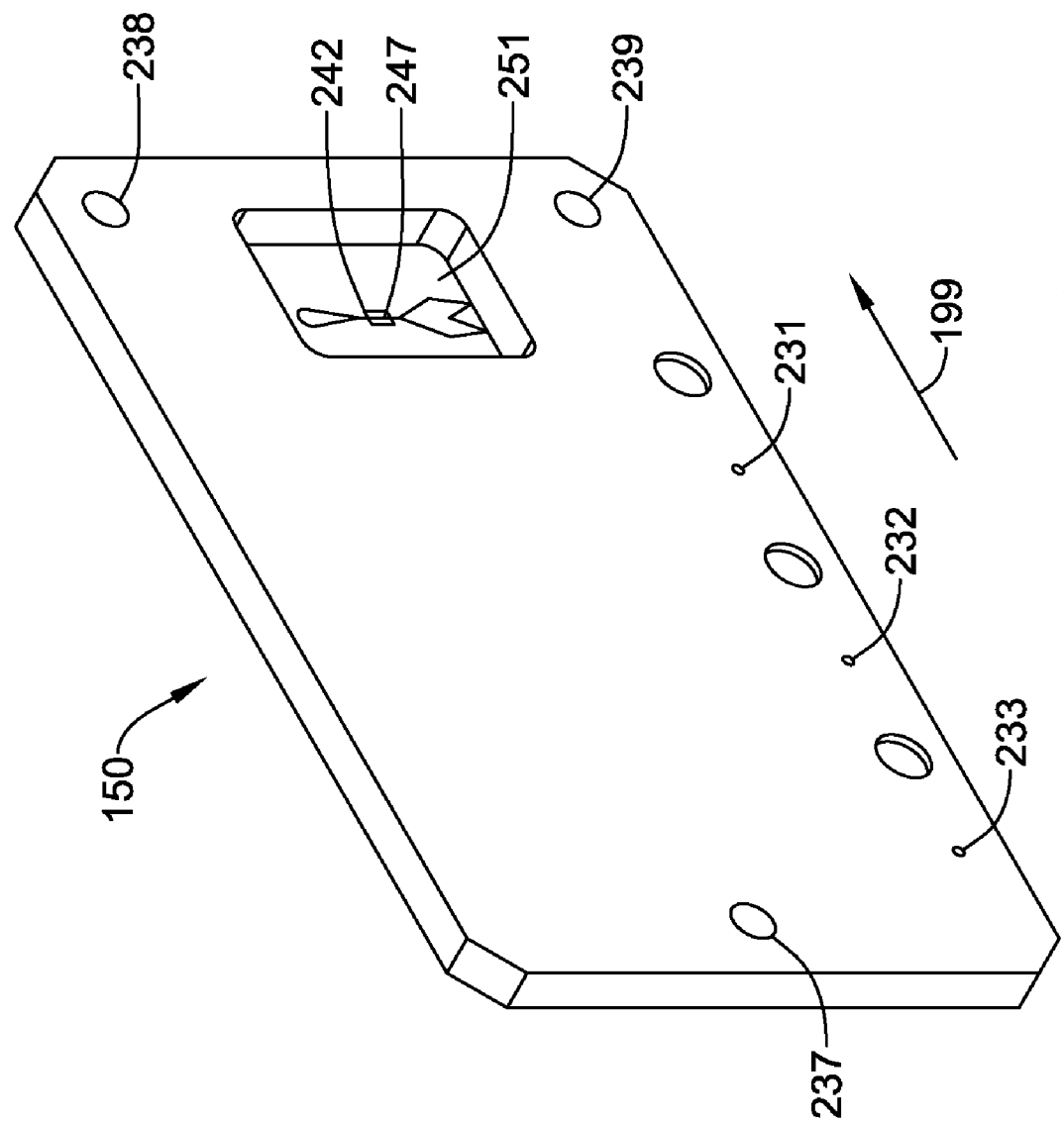
FIG. 15b is a perspective view of the cartridge.
Figure 17:
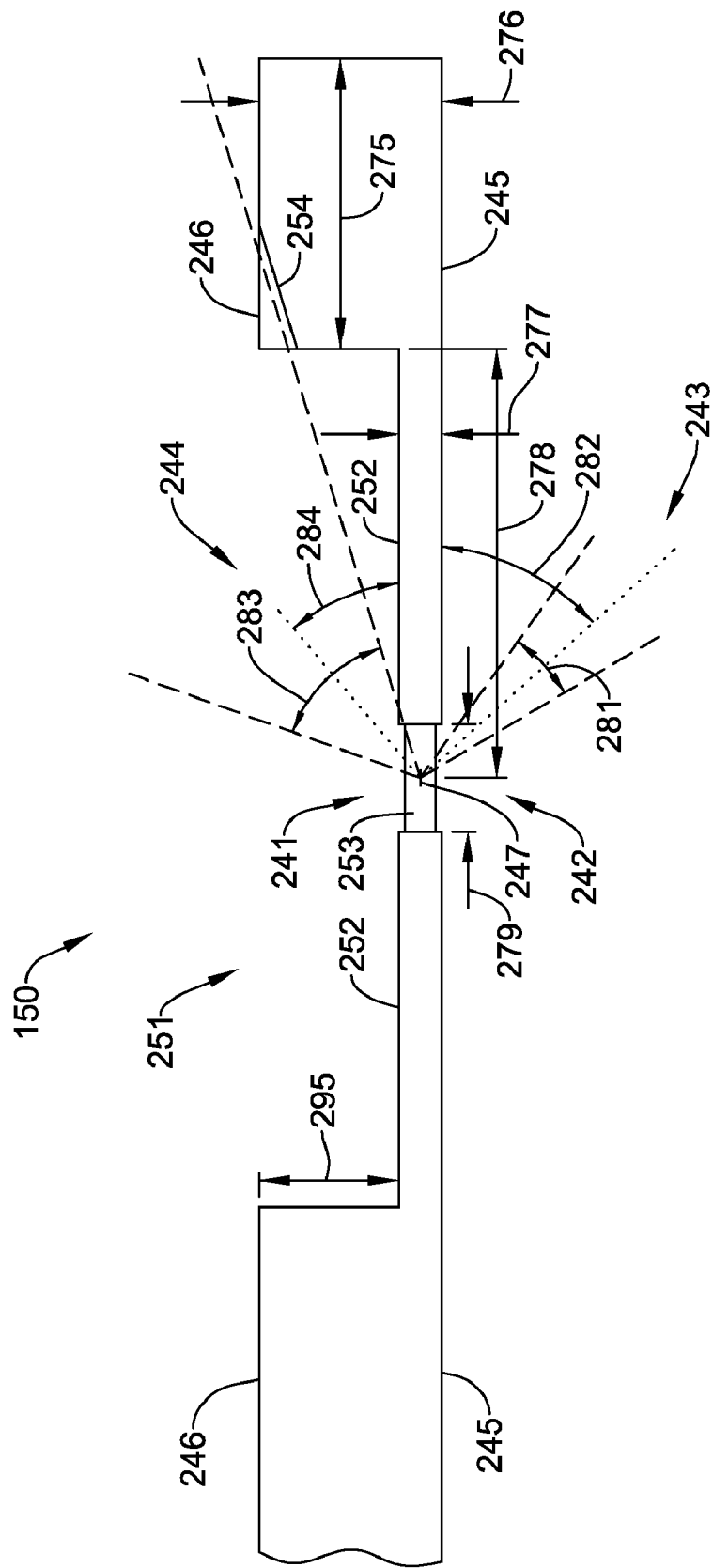
FIG. 17 is the same view as FIG. 16 except with a cone obstruction removed.

Detector cone 244 may have an angle width 283 of about 60 degrees. In other embodiments, the detector cone 244 may have an angle width 283 that ranges up to 65 degrees. The direction 284 of the detector cone relative to the surface 252 may be about 45 degrees. That means the lower portion of detector cone 244 towards the surface 246 may be at about an angle of 15 degrees or so relative to surfaces 246 and 252. The length 275, thicknesses 276, 277 and 295, and lengths 278 and 279 may affect the clearances for the respective cones. The window thickness 277 may be about one-sixty-fourth of an inch, i.e., 0.015625 in. The step or depth 295 of the opening 251 in the cartridge 150 maybe about one-eighth of an inch, i.e., 0.125 in. Many of the dimensions may be available or inferable from FIGS. 14b and 15a. The opening 251 has an edge on one side at the surface 246 and a point at a center of the edge has a distance y or depth 295 to the surface 252 along a line approximately perpendicular to the surface 246. The point has a distance z from the edge along a straight line in the opening 251 to the target area or flow channel 247. The ratio of y/z may be less than 0.3. In other embodiments, the ratio of y/z is less than 0.26. Detector cone 244 has a vertex situated at the target area. The vertex angle may have a cosine greater than 0.1. In other embodiments, the vertex angle may have a cosine equal to or greater than 0.5. Since the flow channel 247 is close to surface 252 and the angle of cone 244 is wide and the direction of the cone is significantly to one side, the cone 244 may encounter an obstruction at the edge of opening 251 on or near the surface 246. This obstruction may prevent some light having significant data from being detected from cone 244. Some of the light being provided to the flow channel 247 may be occluded. This obstruction may prevent proper illumination of the flow channel. The consequence may include detected signals with low signal to noise ratios or no signals which may have been present were it not for the obstruction. If y/z is not less than 0.26, and in some embodiments, not less than 0.2, the obstruction may be eliminated by removing some of the material from the surface 246 of the cartridge 150 at the edge of the opening 251 to make a clearance for cone 244 at a new surface 254, thus increasing z as shown in FIG. 17.

Figure 18:
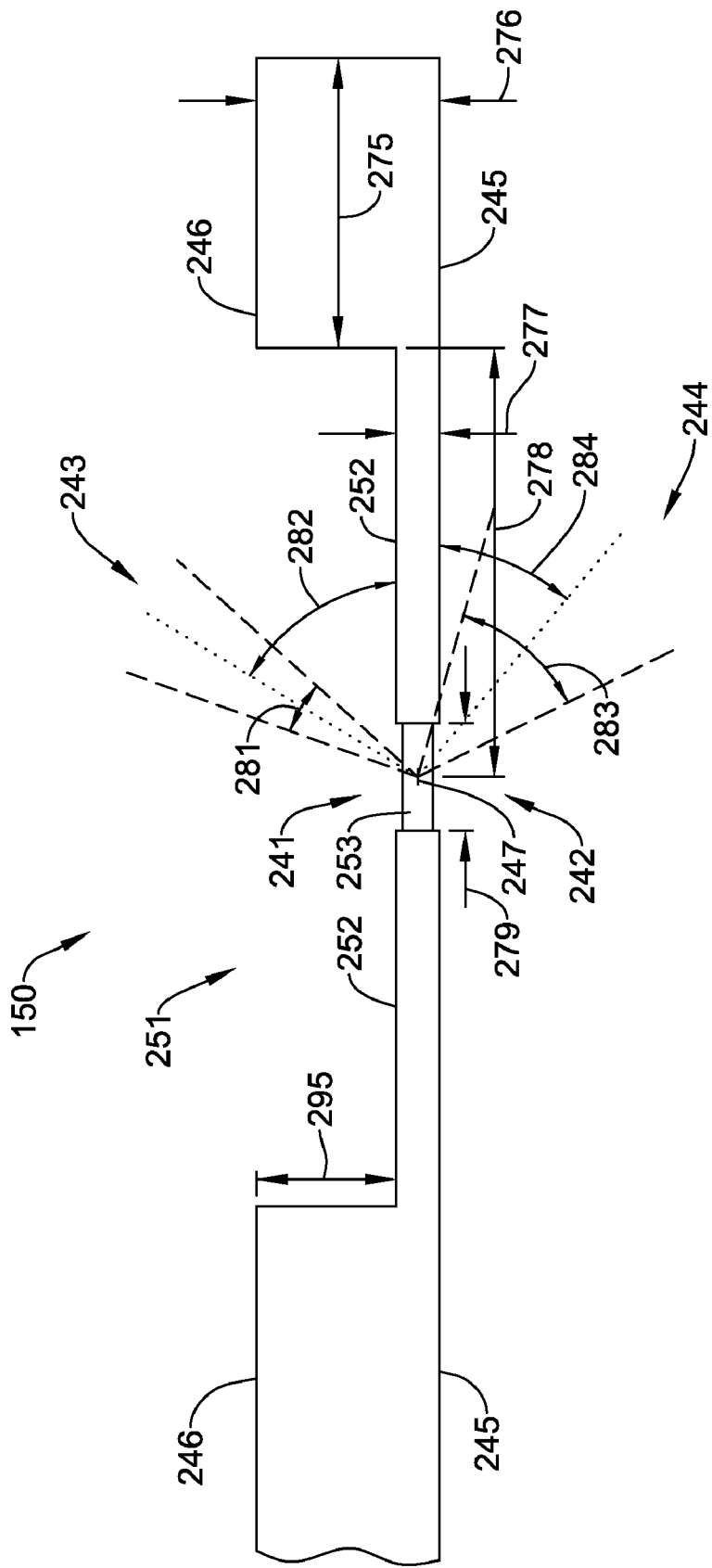
FIG. 18 is the same view as FIG. 16 except the positions of the detector and the source are reversed along with their corresponding cones.

Another approach to the detector cone 244 obstruction issue may be to swap the positions of the light source and detector with the corresponding cones 243 and 244, respectively, as shown in FIG. 18. Then source cone 243 may be facing window 241 proximate to surface 252 of opening 251. With the direction of the source cone 243 relative to the surface 252 being at an angle 282 of about 45 degrees and the cone 243 having an angle of 281 about 20 degrees wide, the portion the cone 243 closest to surface 252 may be at an angle of about 35 degrees relative to a plane parallel to the surfaces 246 and 252. It is apparent that the source cone 243 easily clears the edge of the opening 251 proximate to surface 246 of the cartridge 150. On the other side of the cartridge having surface 245, the wide detector cone 244 appears to encounter no obstruction relative to window 242 and surface 245 of the cartridge 150. The reason apparently is that the flow channel 247 and its encompassing structure of thin films 253 are so close the surface 245 that there is virtually no obstruction from a small edge of window 242.

Figure 19:
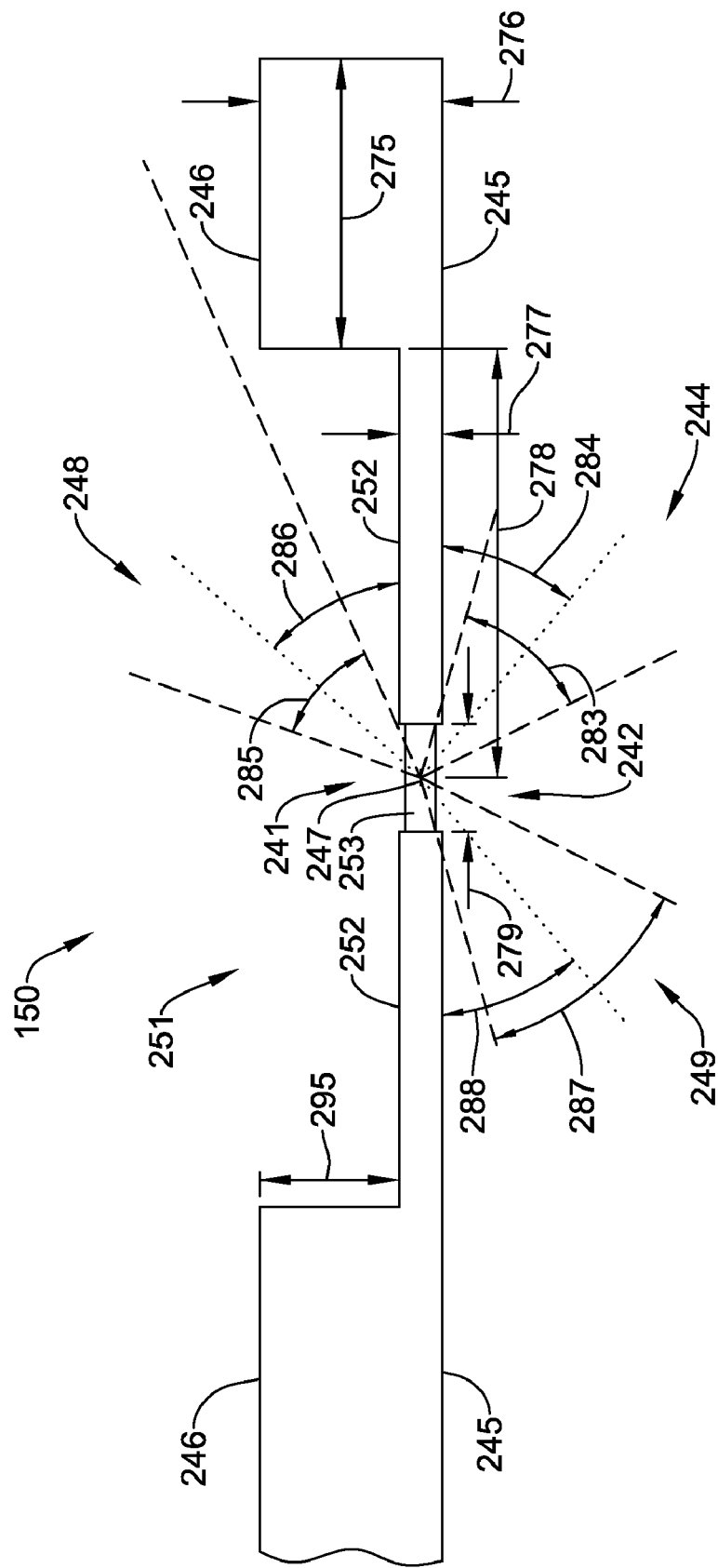
FIG. 19 is the same view as FIG. 16 except it has a multiple detector cone arrangement.

If the 20 degree source cone 243 is replaced with a 45 degree angle 285 or greater source cone 248 at window 241, as shown in FIG. 19; there might be a slight obstruction of the cone 248 at the edge of the opening 251 at surface 246, if cone 248 were rotated further to the right than illustrated by an angle 286 in the Figure. If this obstruction or occluding occurred, it may be cleared by removing some of the material from the cartridge 150 at the edge of the opening 251 and surface 240, as shown in FIG. 17. Also added may be a 30 degree angle 287 detector cone 249 for detecting scattered light and/or direct light. Cone 249 direction angle 288 may be about 45 degrees. In the configuration of FIG. 19, detector cone 244 appears situated adequately in that no obstruction is apparent.

Figure 21:
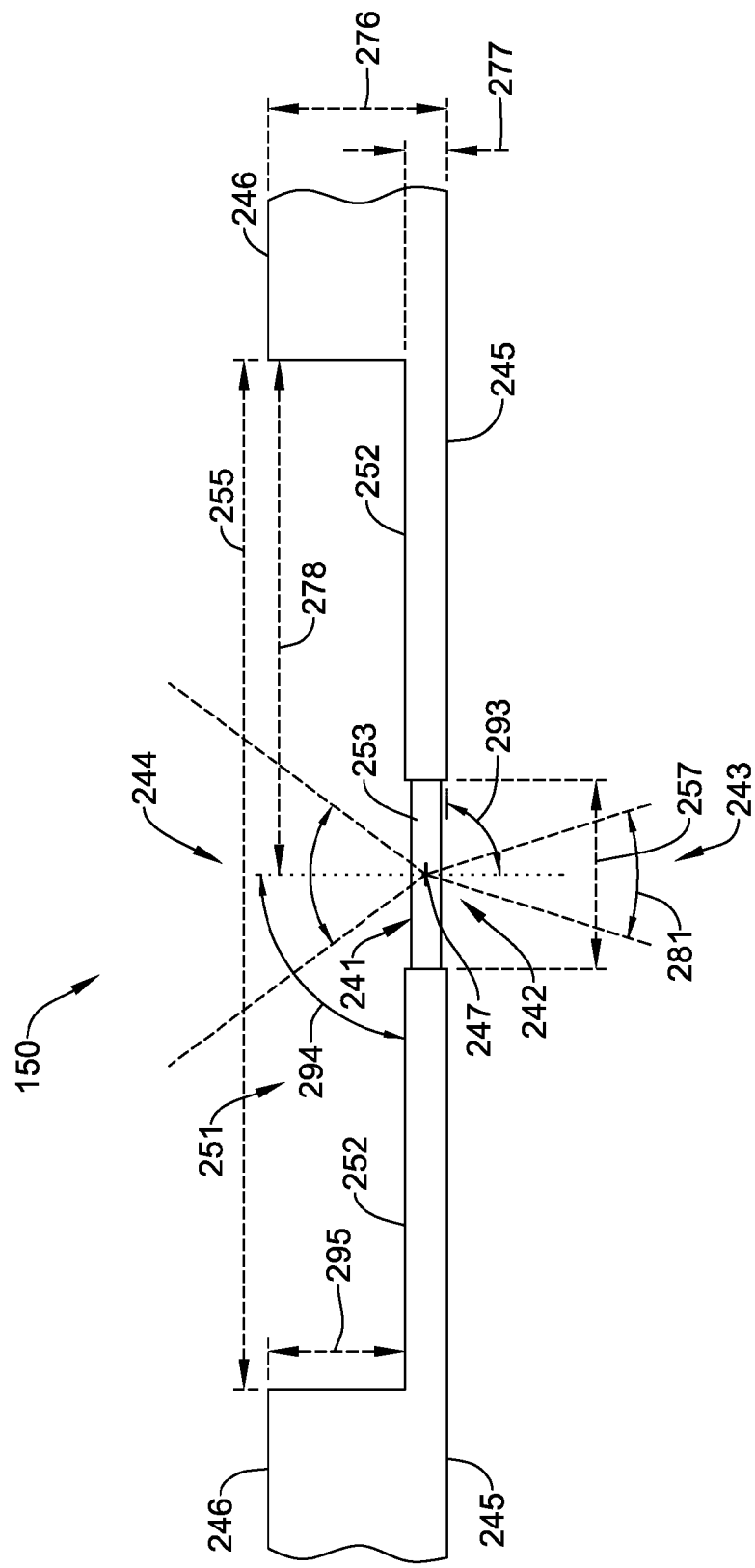

However, several other approaches that do not involve removal of cartridge 150 material for any of wide cone arrangements may solve the above-noted obstruction issues. One is to turn the orientation of the cut-out opening 251 in the plane of surface 246 about 90 degrees clockwise or counterclockwise relative to the source and detector cones. The dimensions 255 and 256 of the opening 251 may be approximately about 15 by 20 millimeters, respectively. The dimensions 257 and 258 of window 241, 242 may be approximately 2 by 5 millimeters, respectively. The dimensions may have different values. Dimensions 289 and 291 may be calculated. FIG. 21 shows the shorter dimension 255 parallel to the direction of the slant of the cones 243, 244, 248 and 249, along the length of flow channel 247. Thus, in FIG. 21, the orientation angles 293 and 294 of cones 243 and 244, respectively, may be about 90 degrees. This orientation of the flow channel 247 is also evident in FIGS. 16-19. The turning the opening 251 about 90 degrees may put the longer dimension 256 (about 33 percent longer) of the opening 251 and the direction of the flow channel 247 approximately parallel to the cone slants so as to provide more clearance relative to the edge of the opening 251 at surface 246 to avoid being be an obstruction or occlusion to, for instance, cones 244 or 248 at an edge of the surface 246 on the side of cartridge 150.

Figure 20:
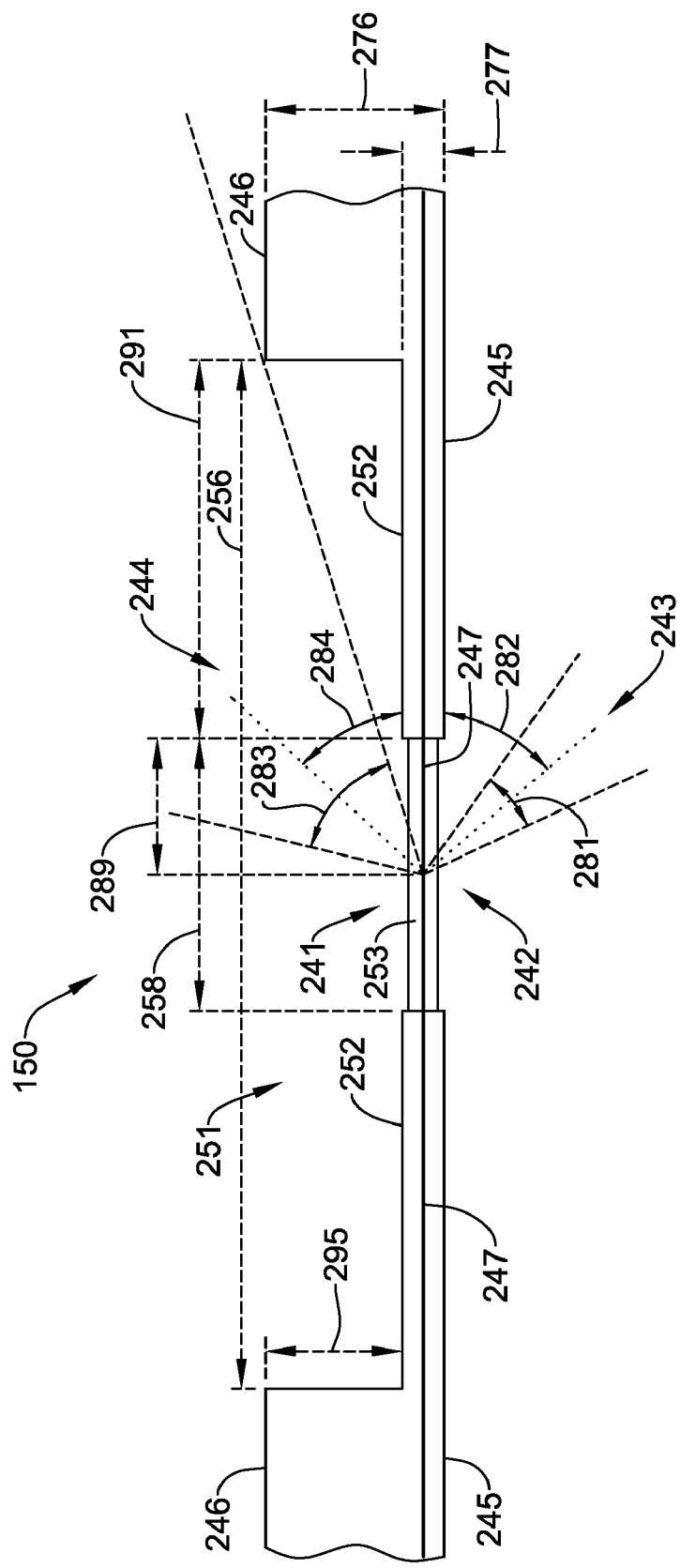
FIGS. 20 and 21 show the cartridge rotated about 90 degrees relative to the positions of the detector and source in comparison to FIG. 16.

FIGS. 20 and 21 show the source cone 243 and detector 244 configuration of FIG. 16 accommodated by the longer dimension 256 of opening 251, which may be accomplished as noted above. The approach here would involve shifting the orientation of the slants of the axes of the source and detector cones 243, 244, 248 and 249 to be towards the direction of the flow channel 247. FIG. 21 is an end view of a cross-section of opening 251. Contrary to FIGS. 20 and 21, FIGS. 16-19 show the angles of the detector and source cones as transverse to the direction of the flow channel 247. FIGS. 16-21 are not necessarily drawn to scale.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A microfluidic cartridge comprising:
a first member having a first surface and a second surface approximately parallel to each other and at a first distance from each other;
a second member having a first surface and a second surface approximately parallel to each other and at a second distance from each other; and
wherein:
the second surface of the first member is situated on the first surface of the second member;
the second member has a target area at the first surface;
the first member has an opening from the first surface through the second surface;
the opening is located over the target area; and
a cone having a vertex situated at the target area, the cone having a vertex angle with a cosine greater than 0.1.

2. The cartridge of claim 1, wherein:
the opening has an edge on one side at the first surface of the first member;
a point at a center of the edge has a distance y to the first surface of the second member along a line approximately perpendicular to the first surface of the second member; and
the point has a distance z from the edge along a straight line in the opening to the target area.

3. The cartridge of claim 2, wherein y/z is less than 0.3.

4. The cartridge of claim 3, wherein y/z is less than 0.26.

5. The cartridge of claim 3, wherein:
the cone has a vertex angle with a cosine equal to or greater than 0.5; and
the cone has a direction of about 45 degrees relative to the first surface of the second member.

6. The cartridge of claim 5, wherein if y/z is not less than 0.26, then a portion of material of the first member proximate to the point at the edge is removed to increase z.

7. The cartridge of claim 1, wherein the cone has a direction approximately 45 degrees relative to the second surface of the second member.

8. The cartridge of claim 6, wherein the target area is in a flow channel having a flow direction.

9. The cartridge of claim 8, wherein:
the opening has a width dimension and a length dimension parallel to the first surface of the first member; and
the length dimension is greater than the width dimension.

10. The cartridge of claim 9, wherein:
the cone has a portion closest to the edge; and
the edge is approximately perpendicular to the flow direction.

11. The cartridge of claim 10, wherein:
the cone has a portion closest to the edge; and
the edge is approximately parallel to the flow direction.

12. The cartridge of claim 3, wherein:
the cone has a portion closest to the edge; and
a direction of the cone is tilted approximately in a direction parallel to the flow direction.

13. The cartridge of claim 12, wherein:
y/z is less than 0.2; and
a portion of material of the first member proximate to the point at the edge is removed to increase z.

14. A cartridge comprising:
a first layer having a target area on a first surface; and
a second layer situated on the first surface of the first layer; and
wherein:
the second layer has an opening to the target area;
the opening has a location on an upper edge at a distance y from the first surface along a straight line approximately perpendicular to the first surface;
the point is at a distance z along a straight line in the opening to the target area; and y/z<0.3.

15. The cartridge of claim 14, wherein y/z<0.26.

16. The cartridge of claim 14, wherein:
the target area is in a flow channel; and
a detector having a cone of detection with an apex focused on the flow channel via the open area.

17. The cartridge of claim 16, wherein:
the first layer has a second surface opposite of the first surface of the first layer;
the flow channel is optically accessible from the second surface; and
a source having a cone of radiation focused on the flow channel via the second surface.

18. The cartridge of claim 17, wherein the cartridge has a fluidic circuit connected to the flow channel.

19. A cartridge comprising:

a layer having a first surface and a second surface; and wherein:

the first surface is approximately parallel to the second surface;

the first surface has an opening into the first layer;

a target area is situated in the opening;

the opening has a point on an upper edge of the first surface;

the point has a distance y to a plane along a line approximately perpendicular to the plane;

the plane is approximately parallel to the second surface and intersects the target area;

the point has a distance z along a straight line in the opening to the target area; and y/z<0.3.

20. The cartridge of claim 19, wherein y/z<0.26.

21. The cartridge of claim 19, wherein:

the detector cone is focused on the target area through the opening;

the detector cone has a central axis intersecting the target area via the opening; and the detector cone has a cone angle that ranges up to 65 degrees.

22. The cartridge of claim 21, wherein:

the target area is optically accessible from the first surface; and a light source has a source cone focused on the target area via the first surface.

23. The cartridge of claim 22, wherein the source cone has a cone angle that ranges up to 50 degrees.

24. The cartridge of claim 23, wherein:

the cartridge is a removable media of a particle analyzer; and the target area is in a flow channel of the particle analyzer.

25. The cartridge of claim 24, wherein the cartridge further comprises a fluidic mechanism.

26. The cartridge of claim 25, wherein the flow channel is for containing a core stream of particles which emit light when impinged by light from the light source.

* * * * *